United States Patent
Liu et al.

(10) Patent No.: US 10,488,394 B2
(45) Date of Patent: Nov. 26, 2019

(54) WAFER-SCALE ASSEMBLY OF INSULATOR-MEMBRANE-INSULATOR DEVICES FOR NANOPORE SENSING

(71) Applicant: Ontera Inc., Santa Cruz, CA (US)

(72) Inventors: Xu Liu, Santa Cruz, CA (US); Yuning Zhang, Montreal (CA); William B. Dunbar, Santa Cruz, CA (US)

(73) Assignee: Ontera Inc., Santa Cruz, CA (US)

( * ) Notice: Subject to any disclaimer, the term of this patent is extended or adjusted under 35 U.S.C. 154(b) by 0 days.

(21) Appl. No.: 16/083,997

(22) PCT Filed: Mar. 20, 2017

(86) PCT No.: PCT/US2017/023149
§ 371 (c)(1),
(2) Date: Sep. 11, 2018

(87) PCT Pub. No.: WO2017/165267
PCT Pub. Date: Sep. 28, 2017

(65) Prior Publication Data
US 2019/0120816 A1    Apr. 25, 2019

Related U.S. Application Data

(60) Provisional application No. 62/311,294, filed on Mar. 21, 2016, provisional application No. 62/356,303, filed on Jun. 29, 2016.

(51) Int. Cl.
*G01N 27/327* (2006.01)
*G01N 33/487* (2006.01)
(Continued)

(52) U.S. Cl.
CPC .. *G01N 33/48721* (2013.01); *B01L 3/502707* (2013.01); *B01L 3/502715* (2013.01);
(Continued)

(58) Field of Classification Search
CPC .................................................. G01N 33/48721
See application file for complete search history.

(56) References Cited

U.S. PATENT DOCUMENTS 6,267,872 B1    7/2001    Akeson et al.
6,362,002 B1    3/2002    Denison et al.
(Continued)

FOREIGN PATENT DOCUMENTS

EP          2083015 B1    4/2016
WO    WO 2018/093976 A1    5/2018
(Continued)

OTHER PUBLICATIONS

Yin et al., "Structure of the cold- and menthol-sensing ion channel TRPM8," Science 359, 237-241 (2018) (Year: 2018).*
(Continued)

*Primary Examiner* — Alexander S Noguerola
(74) *Attorney, Agent, or Firm* — Fenwick & West LLP

(57) ABSTRACT

Described herein are nanopore devices as well as methods for assembling a nanopore device including one or more nanopores that can be used to detect molecules such as nucleic acids, amino acids (proteins), and the like. Specifically, a nanopore device includes an insulating layer that reduces electrical noise and thereby improves the sensing resolution of the one or more nanopores integrated within the nanopore device.

25 Claims, 31 Drawing Sheets

(51) Int. Cl.
   *B01L 3/00* (2006.01)
   *G01N 27/447* (2006.01)

(52) U.S. Cl.
   CPC .. *G01N 27/44791* (2013.01); *B01L 2200/025* (2013.01); *B01L 2200/027* (2013.01); *B01L 2200/14* (2013.01); *B01L 2300/0645* (2013.01)

(56) References Cited

U.S. PATENT DOCUMENTS

| | | | |
|---|---|---|---|
| 6,428,959 | B1 | 8/2002 | Deamer |
| 6,464,842 | B1 | 10/2002 | Golovchenko et al. |
| 6,627,067 | B1 | 9/2003 | Branton et al. |
| 6,783,643 | B2 | 8/2004 | Golovchenko et al. |
| 6,936,433 | B2 | 8/2005 | Akeson et al. |
| 7,060,507 | B2 | 6/2006 | Akeson et al. |
| 7,189,503 | B2 | 3/2007 | Akeson et al. |
| 7,258,838 | B2 | 8/2007 | Li et al. |
| 7,347,921 | B2 | 3/2008 | Barth et al. |
| 8,696,881 | B2 | 4/2014 | Blick |
| 9,745,625 | B2 | 8/2017 | Chan |
| 2002/0072164 | A1 | 6/2002 | Umotoy et al. |
| 2002/0094526 | A1 | 7/2002 | Bayley et al. |
| 2003/0005967 | A1 | 1/2003 | Karp |
| 2003/0104428 | A1 | 6/2003 | Branton et al. |
| 2003/0136679 | A1* | 7/2003 | Bohn .................... B01D 57/02 204/543 |
| 2011/0193270 | A1 | 8/2011 | Tan |
| 2011/0227558 | A1* | 9/2011 | Mannion ................ B82Y 30/00 324/71.1 |
| 2012/0182548 | A1 | 7/2012 | Harb et al. |
| 2012/0326247 | A1 | 12/2012 | Dang et al. |
| 2013/0147461 | A1* | 6/2013 | Schmidt .................... C07F 9/22 324/76.11 |
| 2013/0233709 | A1* | 9/2013 | Dunbar ............ G01N 33/48721 204/451 |
| 2014/0147880 | A1 | 5/2014 | Ingber et al. |
| 2015/0316504 | A1* | 11/2015 | Royyuru ........... B01L 3/502761 204/452 |
| 2018/0155768 | A1 | 6/2018 | Cohen et al. |

FOREIGN PATENT DOCUMENTS

| | | |
|---|---|---|
| WO | WO 2019/060042 A1 | 3/2019 |
| WO | WO 2019/060052 A1 | 3/2019 |
| WO | WO 2019/060168 A1 | 3/2019 |
| WO | WO 2019/060172 A1 | 3/2019 |

OTHER PUBLICATIONS

Patent Cooperation Treaty, International Search Report and Written Opinion of the International Searching Authority, International Patent Application No. PCT/US2017/023149, 19 Pages, dated Jul. 27, 2017.
Bayley, H. et al., "Resistive-Pulse Sensing—From Microbes to Molecules," Chem. Rev., 2000, vol. 100, pp. 2575-2594.
Deamer, D.W. et al., "Characterization of Nucleic Acids by Nanopore Analysis," Acc. Chem. Res., 2002, vol. 35, pp. 817-825.
Howorka, S. et al., "Kinetics of duplex formation for individual DNA strands within a single protein nanopore," PNAS, Nov. 6, 2001, vol. 98, No. 23, pp. 12996-13001.
Kasianowicz, J.J. et al., "Nanometer-scale pores: Potential applications for analyte detection and DNA characterization," Disease Markers, 2002, vol. 18, pp. 185-191.
Kasianowicz, J.J. et al., "Simultaneous Multianalyte Detection with a Nanometer-Scale Pore," Anal. Chem., 2001, vol. 73, pp. 2268-2272.
Kasianowicz, J.J.et al., "Characterization of individual polynucleotide molecules using a membrane channel," Proc. Natl. Acad. Sci., Nov. 1996, vol. 93, pp. 13770-13773.
Li, J. et al., "DNA molecules and configurations in a solid-state nanopore microscope," Nature Materials, Sep. 2003, vol. 2, pp. 611-615.
Li, J. et al., "Ion-beam sculpting at nanometre length scales," Nature, 2001, vol. 412, No. 6843, pp. 166-169.
Meller, A., "Dynamics of polynucleotide transport through nanometre-scale pores, Journal of Physics: Condensed Matter," 2003, vol. 15, pp. R581-R607.
Meller, A. et al., "Voltage-Driven DNA Translocutions through a Nanopore," Physical Review Letters, Apr. 9, 2001, vol. 86, No. 15, pp. 3435-3438.
Sauer-Budge, A.F. et al., "Unzipping Kinetics of Double-Stranded DNA in a Nanopore," Physical Review Letters, 2003, vol. 90, No. 23, pp. 238101-1-238101-4.
Vercoutere, W. et al., "Biosensors for DNA sequence detection," Current Opinion in Chemical Biology, 2002, vol. 6, pp. 816-822.

\* cited by examiner

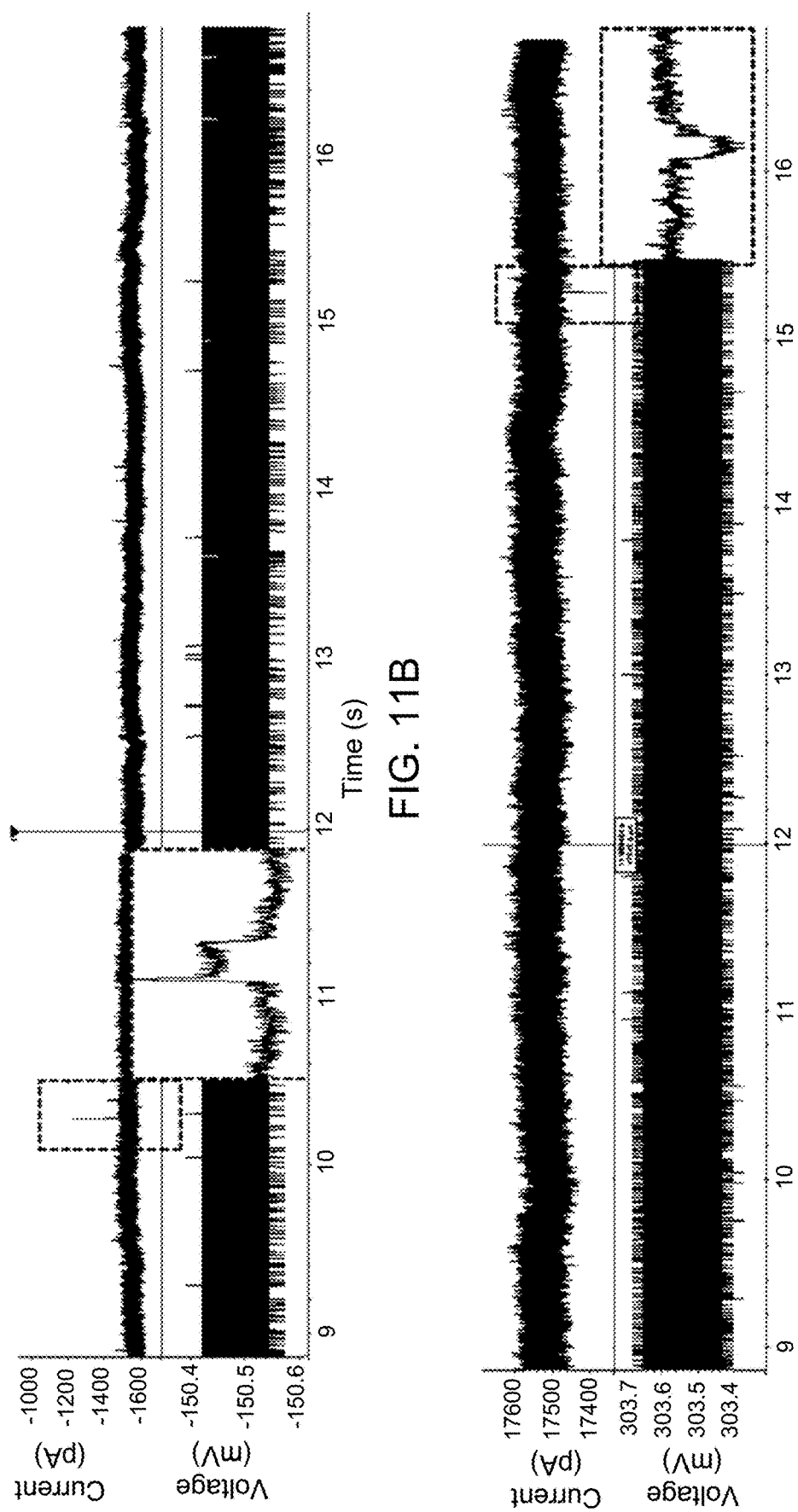

US 10,488,394 B2

WAFER-SCALE ASSEMBLY OF INSULATOR-MEMBRANE-INSULATOR DEVICES FOR NANOPORE SENSING

CROSS REFERENCE TO RELATED APPLICATIONS

This application is the National Stage of International Application No. PCT/US2017/023149, filed Mar. 20, 2017, which claims priority to U.S. Provisional Application No. 62/311,294 filed on Mar. 21, 2016 and U.S. Provisional Application No. 62/356,303 filed on Jun. 29, 2016. The content of each of the above referenced applications is incorporated by reference in its entirety.

BACKGROUND

Detecting nucleic acids specific to an organism in an accurate and efficient way can be invaluable for identifying microbes, viruses, and other infection agents. Detecting specific proteins and nucleic acids can also be a way to detect and track the progression of diseases.

Solid-state nanopores provide a simple nucleic acid sensor. Nanopore devices can in principle be made inexpensively and incorporated into small form factors for portable and disposable use. Solid-state nanopores detect molecules by applying a voltage across the pore, and measuring ionic current flow the through pore. The current impedance changes when individual molecules pass through the nanopore, and these are referred to "events." The overall efficacy of any given nanopore device depends on its ability to accurately and reliably measure impedance events above noise, and to discriminate events that are due to molecules of interest from events due to any background molecules when present.

Experiments published in the literature have demonstrated the detection of DNA, RNA and proteins that pass one at a time through a nanopore. Typically, a nanopore is formed in an insulating membrane by drilling with an electron or ion beam, or etching, or by the action of high voltages for controlled dielectric breakdown. Such nanopore devices that include the membrane and nanopore and inserted into a separate fluidic cell are commonly made from plastics.

BRIEF DESCRIPTION OF THE DRAWINGS

FIG. 11A-C depicts combined optical imaging and electrical nanopore sensing using an example nanopore device.

Figure 1A:
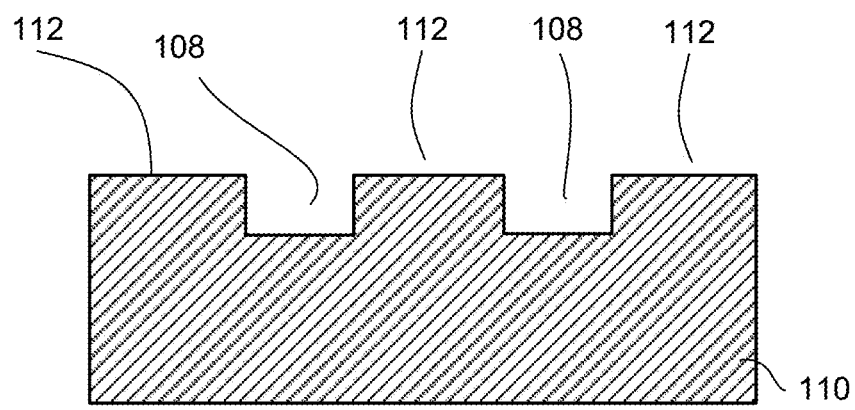
FIG. 1A is a cross sectional view of a first insulating substrate including features on a surface of the first insulating substrate, according to one embodiment.

The figures use like reference numerals to identify like elements. A letter after a reference numeral, such as "308a," indicates that the text refers specifically to the element having that particular reference numeral. A reference numeral in the text without a following letter, such as "308," refers to any or all of the elements in the figures bearing that reference numeral (e.g. "channels 308" in the text refers to reference numerals "channel 308a" and/or "channel 308b" in the figures).

DETAILED DESCRIPTION

Introduction

This description presents a number of methods for forming a nanopore device that includes fluidic interfaces to a single or multiple nanopore sensor array, where the methods include the formation of the interfaces themselves. That is, the final nanopore device is fabricated in a single overall process. This description also presents various designs for nanopore devices, and the measurement systems in which they are included.

Embodiments described herein include a process for fabricating a nanopore device with one or more fluidic channels within the nanopore device as part of the fabrication flow process. Importantly, the method uses insulating materials that reduce electrical noise and thereby improve the sensing resolution of the one or more nanopores integrated into the nanopore device. By integrating the fluidic paths (i.e., fluid channels) into the nanopore device itself, the design of components, such as a flow-cell housing, that interface with the nanopore device (e.g., to introduce sample molecules/reagents to be measured) can be simplified. The process also improves the ability to tailor such a nanopore device to possess an increased number of nanopores per nanopore device (e.g., for multi-pore sensing) relative to existing nanopore structures, while minimizing the total size (footprint) of the device. These collective advantages (integration of the channel paths, low noise feature of the channel path materials, the multiple-pores-per-chip capability of the process flow) can all be realized using wafer-scale processes, resulting in the highest possible sensor density at the lowest possible cost.

The methods described herein can create nanopore devices at wafer scale. Wafer-scale production techniques are used that sandwich the nanopore-containing membrane(s) between insulating material substrates. Channels are created in the insulating layers to enable fluidic and electrical access of each nanopore. By varying the micro-loading channel design in the insulating layer, devices can be single pore or multi-pore arrayed implementations. Devices can also be dual-pore devices, with one or more membranes, that enable two-pore control. The nanopore devices allow for optical and electrical sensing simultaneously, where each nanopore is separately electrically addressable. The channels are embedded in insulating substrate, which reduces electrical noise. Altogether, the nanopore device combines fabrication of both the channels within the insulating layer and one or more nanopore-containing membranes as a single process that produces directly useable units with optimal noise performance.

The accompanying description is divided into 8 sections:

Section 1: Describes an overview of the fabrication process for generating a membrane layer bound to an insulating layer, according to one embodiment.

Section 2: Describes an alternate fabrication process, according to one embodiment.

Section 3: Describes an example of a two channel/single membrane device implementation of the process.

Section 4: Describes an example of a two channel/dual membrane device implementation of the process.

Section 5: Describes a multi-pore array device implementation of the process.

Section 6: Describes one possible technique for improving the mechanical robustness of the device.

Section 7: Describes a measurement system that includes the nanopore device within a flow-cell housing.

Section 8: Example results obtained from the nanopore devices described herein.

I. MANUFACTURING PROCESS OVERVIEW

FIG. 1A is a cross sectional view of a first insulating substrate 110 including features 108, according to one embodiment. The features are created on a surface 112 of the first insulating substrate 110. The first insulating substrate 110 can be glass, such as fused silica, sapphire, borosilicate glass, aluminosilicate glass, quartz, pyrex, etc.

The features include at least one channel 108 which is depicted as an indentation into the surface 112 of the first insulating substrate 110 in FIG. 1A. The geometry of each channel 108 is dictated by the desired fluid flow paths. Generally, the channel geometry is designed such that fluid can be introduced on one end and flow through the fluid channel 108 without any pressure requirements, such that capillary action is sufficient. In some scenarios, an external force or pressure may be required to ensure that fluid flow through the fluid channel 108 occurs. Channels 108 can be made in the first insulating substrate 110 using at least one of a number of techniques, an example of which includes photolithography followed by reactive ion (RIE) etching. Other methods can be used to make the channel deeper. In one embodiment, the depth of any given channel is between the range of 0.1 to 10 μm. I some embodiments, the depth of a channel can range up to 100 μm. In particular embodiments, the depth of a channel is between 1 and 3 μm. Since there is no membrane present at this point in the process, over-etching is not a concern.

Figure 1B:
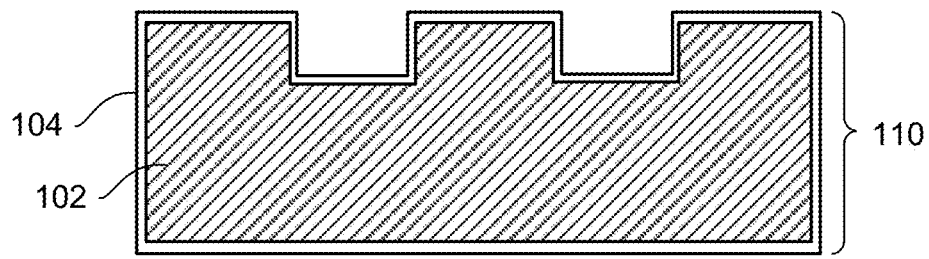
FIG. 1B is a cross sectional view of an alternate embodiment of the first insulating substrate, according to another embodiment.

FIG. 1B is a cross sectional view of an alternate embodiment of the first insulating substrate 110, according to another embodiment. Rather than being made of an insulating material, the substrate can also be made of silicon (or another non-insulating material 102) with insulating coating 104, such as oxide. In this case, the non-insulating substrate 102 is coated by an insulating layer 104 after etching. Using a non-insulating substrate such as silicon can be advantageous because the etching process may be easier and/or less expensive since such materials may be more widely available in nanofabrication. The insulating coating 104 transforms the non-insulating substrate 102 into an insulator, thereby allowing it to serve a similar function as an insulating substrate 110, as illustrated in FIG. 1A, such as glass with regard to electronic properties. As another alternative, two different pieces of silicon substrate may be bonded together to form the features instead of etching a single piece of glass or silicon substrate.

Figure 1C:
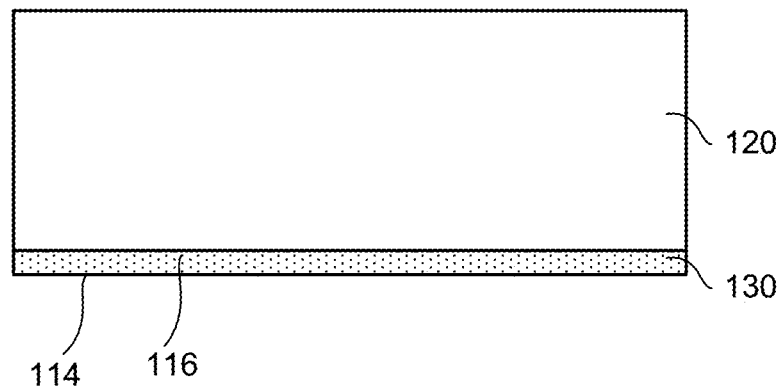
FIG. 1C is a cross sectional view of a second substrate coated on one side with a membrane layer, according to one embodiment.

FIG. 1C is a cross sectional view of a second substrate 120 coated on one side with a membrane layer 130, according to one embodiment. As shown in FIG. 1C, the membrane layer 130 may have a first surface 114 and a second surface 116. In one embodiment, the second substrate 120 is silicon (Si). The thickness of the second substrate 120 may vary. For example, in one embodiment the thickness is between 200-500 μm. The thinner the second substrate 120 is, the faster it can be removed during a later step in the process (e.g., wet etching using potassium hydroxide (KOH)).

The combination of the second substrate 120 and membrane layer 130 facilitates the bonding of the membrane layer 130 to the first insulating substrate 110, which will be described in further detail below. As used hereafter, this structure that facilitates the bonding of the membrane layer 130 to the first insulating substrate will be referred to as the membrane assembly.

In one embodiment, the membrane assembly includes the membrane layer 130 which is coated on the second substrate 120. Specifically, a first surface 114 of the membrane layer is exposed whereas a second surface 116 of the membrane layer is in contact with the second substrate 120. Various deposition techniques may be used to deposit the membrane layer, such as low pressure chemical vapor deposition (LP-CVD) or plasma enhanced chemical vapor deposition (PECV). The membrane layer may be made of a variety of materials. In one embodiment, the membrane layer 130 is made of silicon nitride ($SiN_x$). The thickness of the membrane layer 130 may vary depending upon the specific properties desired. For example, a thicker membrane is stronger mechanically; however, often a better electrical signal (e.g., less noise) can be achieved using a thinner membrane. In one embodiment, the thickness of the membrane layer is between 10-500 nm. In some embodiments, the thickness of the membrane layer is between 20-30 nm.

Figure 1D:
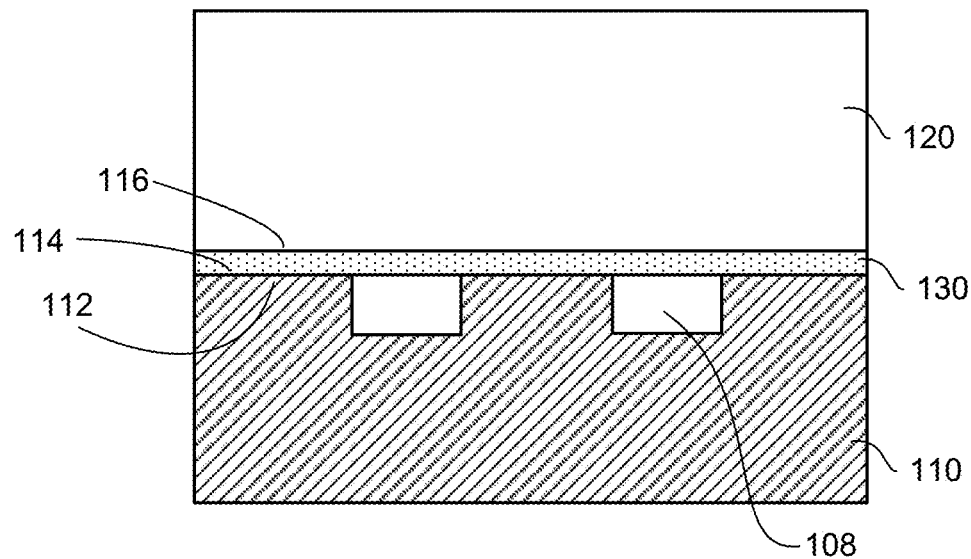
FIG. 1D is a cross sectional view of the first insulating layer bonded to a membrane layer on one side of a second substrate, according to one embodiment.

FIG. 1D is a cross sectional view of the first insulating layer 110 bonded to the membrane assembly through the membrane layer 130, according to one embodiment. The first insulating layer 110 is bonded to the membrane layer 130 on the side/surface 112 of the first insulating layer 110 that includes the channels 108. More specifically, the first surface of 114 of the membrane layer 116 is bonded to the surface 112 of the first insulating layer 112. Any one of a variety of bonding techniques can be used to bond the first insulating layer 110 to the membrane layer 130. Examples of possible bonding techniques include direct bonding, plasma activated bonding, anodic bonding, eutectic bonding, glass frit bonding, adhesive bonding, thermocompression bonding, reactive bonding, transient liquid phase diffusion bonding, etc.

Figure 1E:
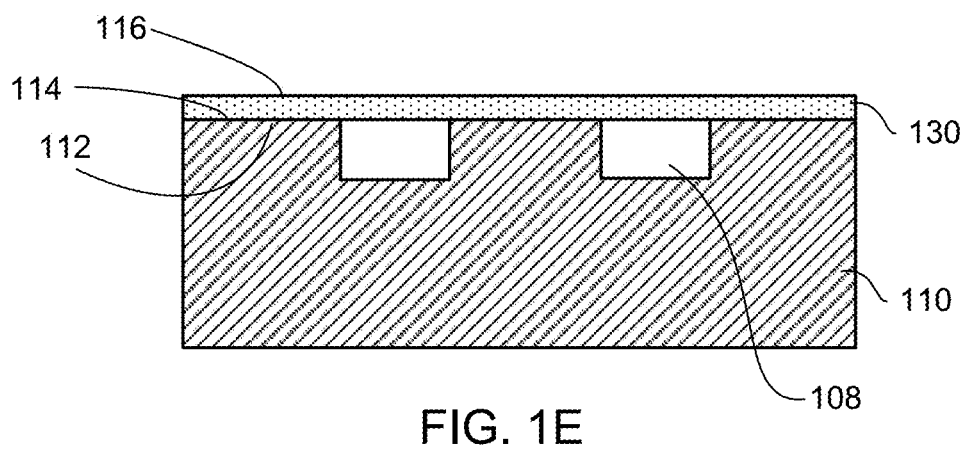
FIG. 1E is a cross sectional view of the membrane layer bonded to the first insulating layer, according to one embodiment.

FIG. 1E is a cross sectional view of the membrane layer 130 bonded to the first insulating layer 110, according to one embodiment. The second substrate 120 is removed from the membrane layer 130, leaving the first insulating layer 110 bonded to the membrane layer 130. More specifically, the first surface 114 of the membrane layer 130 remains bound to the surface 112 of the first insulating layer 112 whereas the second surface 116 of the membrane layer 130 is now exposed. Various techniques may be used to remove the second substrate 120, including etch processes such as KOH or Tetramethylammonium hydroxide (TMAH).

Figure 1F:
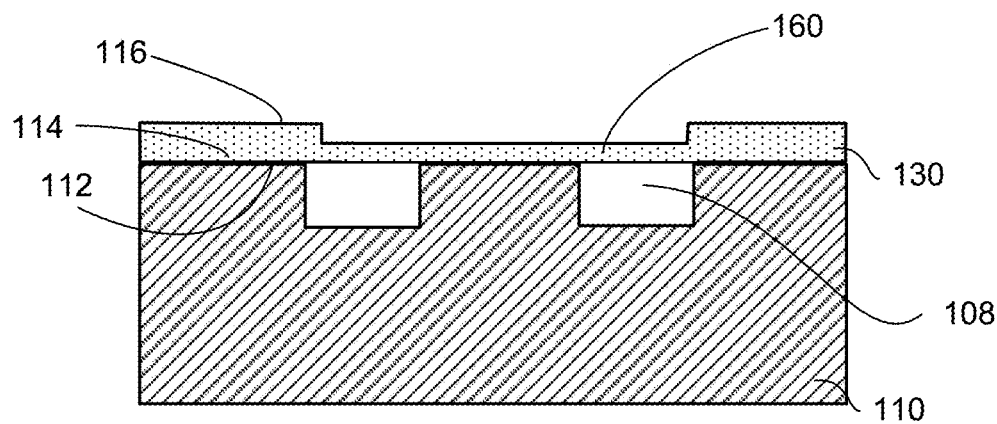
FIG. 1F is a cross sectional view of a thinned membrane layer bonded to the first insulating layer, according to one embodiment.

FIG. 1F depicts a cross sectional view of the membrane layer 130 bonded to the first insulating layer 110 including a thinned portion 160 of the membrane layer 130, according to one embodiment. Thinning the membrane layer 130 can be achieved using one or both of photolithography or reactive-ion etching (RIE). As an example, an open window is patterned and RIE is applied following photolithography to thin down the membrane layer 130 through the open window. In various embodiments, the membrane layer 130 may have a default thickness of 100-300 nm whereas the thinned portion 160 of the membrane layer 130 has a thickness of 10-50 nm.

As depicted in FIG. 1F, the thinned portion of the membrane layer 130 resides above the channels 108. The thinning of the membrane layer 130 can be performed on the exposed second surface 116 of the membrane layer, as shown in FIG. 1F. More specifically, the location of the thinned portion of the membrane layer 130 can be selected such that the subsequent creation of a nanopore in the membrane layer 130 can be performed in the thinned portion of the membrane layer 130. Therefore, the nanopore can be created by penetrating a thinner membrane layer 130. Importantly, the membrane layer 130 retains its default thickness in other locations (e.g., where the membrane layer 130 is bonded to the first insulating substrate 110), thereby maintaining a more mechanically robust membrane layer 130.

II. ALTERNATE MANUFACTURING PROCESS

Figure 2A:
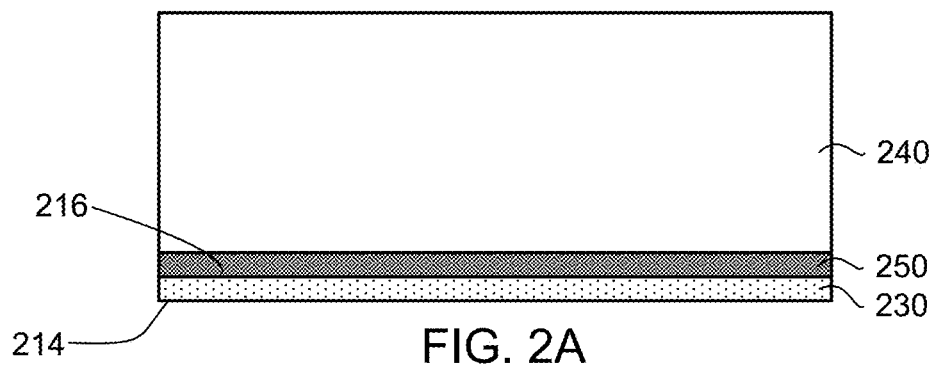
FIGS. 2A-C illustrate an alternative set of steps for manufacturing a membrane layer bonded to the first insulating layer, according to one embodiment.
Figure 2B:
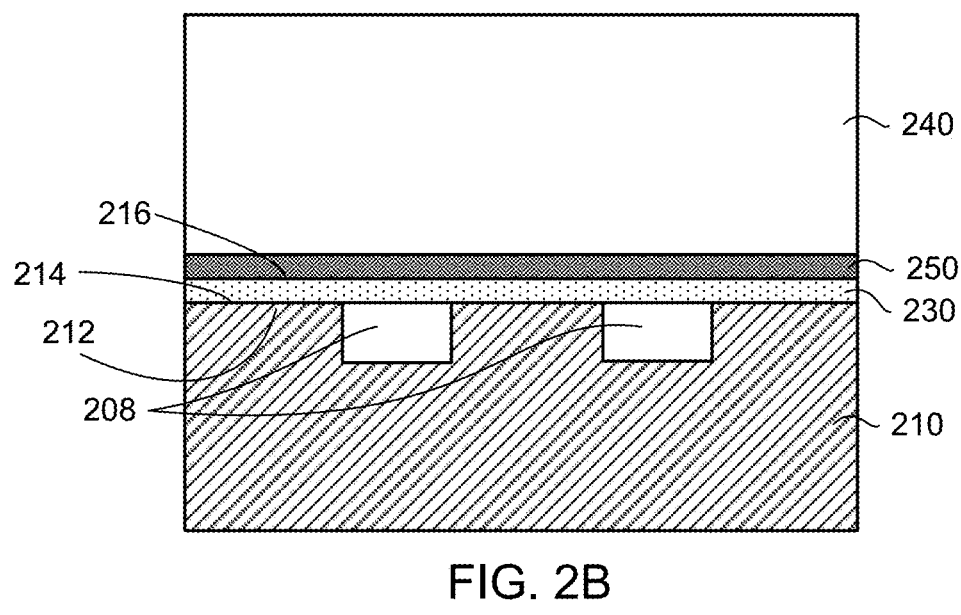
Figure 2C:
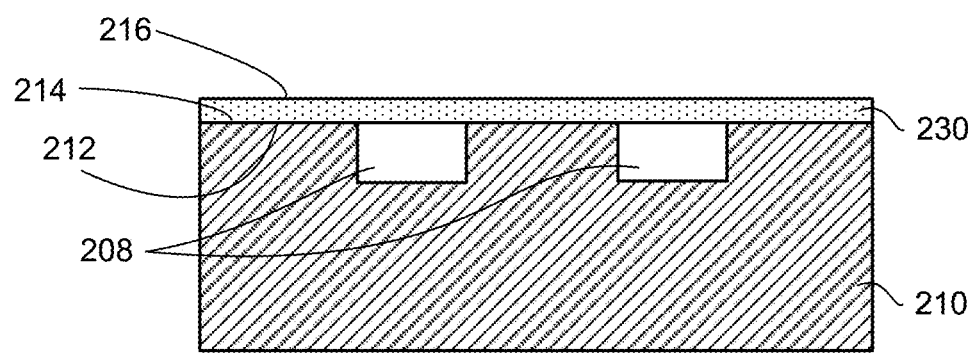

FIGS. 2A-C illustrate an alternative set of steps for manufacturing the membrane layer 230 bonded to the first insulating layer 210, according to one embodiment. In other words, the steps of FIGS. 2A-C are an alternative to the steps for manufacturing the device described with respect to FIGS. 1A-1F.

As illustrated in FIG. 2A, in this alternate process, the membrane layer 230 is formed on a sacrificial layer 250, which is formed on the second substrate 240. Specifically, a first surface 214 of the membrane layer 230 is exposed whereas a second surface 216 of the membrane layer 230 is in contact with the sacrificial layer 250. Here, the combination of the membrane layer 230, sacrificial layer 250, and the second substrate 240 serves as the membrane assembly that facilitates the bonding of the membrane layer 230 to the first insulating layer 210. The material used and thickness of the sacrificial layer 250 may vary. Additionally, the material used for the sacrificial layer 250 affects which materials may be used for membrane layer 230. In one embodiment, the sacrificial layer 250 is silica ($SiO_2$) (e.g., 20 nm thick), and the membrane layer 230 is made of $SiN_x$.

As illustrated in FIG. 2B, the membrane layer 230 is bonded to the first insulating layer 210. Specifically, a first surface 214 of the membrane layer 230 is bonded to the surface 212 of the first insulating layer 210 that includes the channels 208. Additionally, the second surface 214 of the membrane layer 230 remains in contact with the sacrificial layer 250. The bonding of the membrane layer 230 to the first insulating layer 130 be achieved by performing any of the bonding processes as previously disclosed in regards to FIG. 1D. The sacrificial layer 250 and the second substrate 240 are then removed. Therefore, as illustrated in FIG. 2C, the membrane layer 230 remains bonded to the first insulating layer 210 (e.g., through the first surface 214 of the membrane layer 230 and the surface 212 of the first insulating layer 210). The second surface 216 of the membrane layer 230 is exposed.

In various embodiments, the sacrificial layer 250 is removed using a chemical process. The membrane assembly may be exposed to a chemical that selectively removes the sacrificial layer 250. For example, the sacrificial layer 250 can be etched such as with hydrogen fluoride (HF). The etching process may not physically affect the second substrate 240 but due to the removal of the sacrificial layer 250, the second substrate 240 is also detached. In an alternate embodiment, a nickel metal film (e.g., 500 nm thick) can be used as a sacrificial layer 250, and the membrane layer 230 is made of $SiN_x$ or $SiO_2$. In this case, the sacrificial layer 250 is removed using a solution, such as iron (III) chloride ($FeCl_3$), which also detaches the second substrate 240. As above, the end result of this alternate process is the membrane 230 layer bonded to the first insulating layer 210 on the same side as the channels 208. In various embodiments, the membrane layer 230, shown in FIG. 2C, can be thinned at locations where the nanopores are to be generated as was previously described in reference to FIG. 1F.

III. TWO CHANNEL/SINGLE MEMBRANE DEVICE

The end product of a first insulating layer bonded to a membrane layer, as described in sections I and II above, can be used to produce a nanopore device that includes two channels and a single membrane layer. The channels are located in the same plane within the first insulating layer. The two channels permit dual nanopore sensing and control. Here, FIGS. 3A-3G describe the generation of a membrane layer bonded to a first insulating layer 310 that contains a particular set of fluid channels 308, in accordance with the processes described in FIG. 1 and FIG. 2. Further, FIGS. 3H-3O describe the process for forming the nanopore device with the bonded first insulating layer and membrane layer.

Figure 3A:
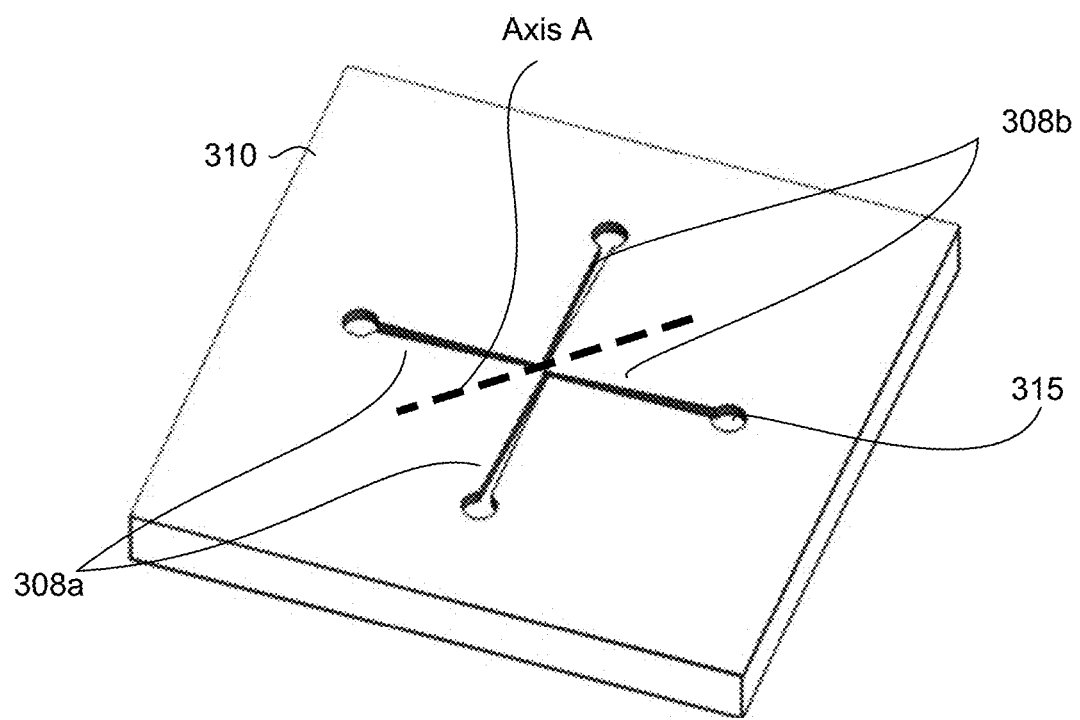
FIGS. 3A-3R illustrate a method for forming a nanopore device that includes two channels and a single membrane layer, according to one embodiment.

FIG. 3A illustrates a first insulating layer 310, according to one embodiment. The first insulating layer 310 includes a first channel 308a and a second channel 308b formed on the surface of the first insulating layer 310. Each channel 308 is formed on the surface of the first insulating layer 310 with a reservoir 315 at either distal end. Each reservoir 315 is coupled to a straight portion of the channel 308 that may be constant in width or may taper in width as the channel 308 progresses towards the midpoint. In one embodiment, the narrowest width of the channel 308 can be 5 µm and the widest width of the channel 308 can be on the order of 500 µm. The diameter of the reservoir 315 can range from approximately 500 µm up to 1 mm or more. For example, in some embodiments, the diameter of the reservoir 315 is 1 centimeter. As depicted in FIG. 3A, each reservoir 315 is circular in diameter. In other embodiments, the reservoir 315 may be a square, rectangular, triangular, oval, hexangular, or another polygon in shape.

Figure 3B:
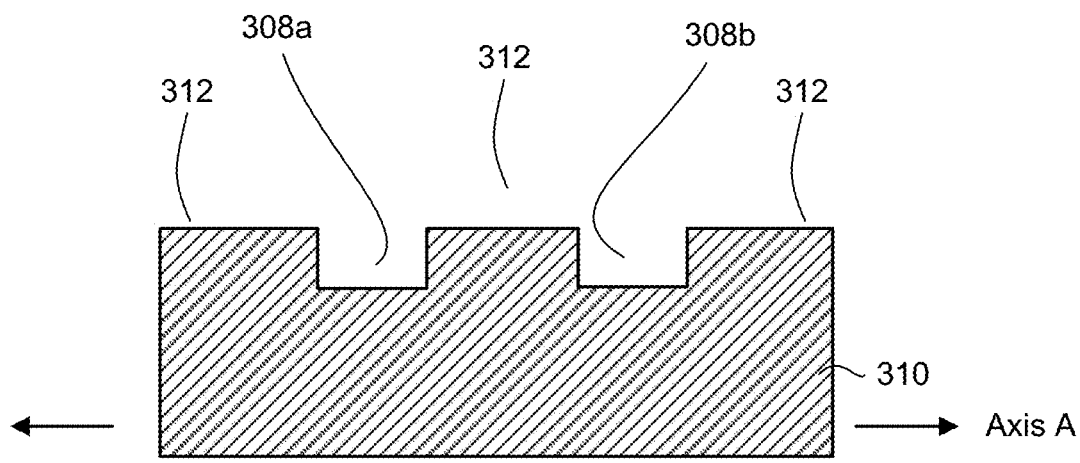

FIG. 3B illustrates a cross sectional view of the first insulating layer 310 of FIG. 3A, according to one embodiment. More specifically, FIG. 3B depicts a cross section view along Axis A as shown in FIG. 3A. Here, the first channel 308a and the second channel 308b may be the closest in distance to one another in the first insulating layer 310. The first insulating layer 310 and channels 308 may be formed as described with respect to FIG. 1A in Section IV above.

Figure 3C:
Figure 3D:
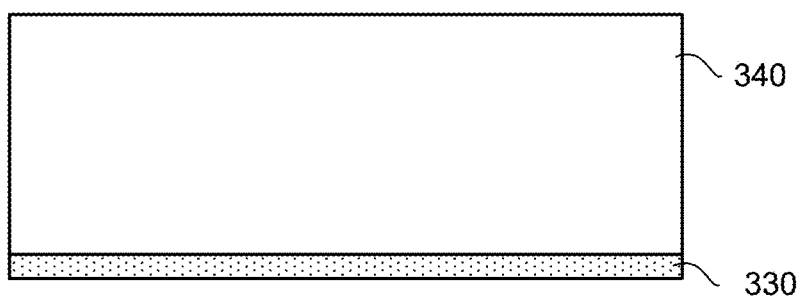

FIGS. 3C and 3D illustrate an example process for attaching a membrane layer 330 to the second substrate 340, according to one embodiment. As illustrated in FIG. 3C, the second substrate 340 is coated on both sides with two membrane layers 330 and 331. This process may be, for example, low pressure chemical vapor deposition (LPCVD) of silicon nitride (SiN$_x$), however more examples are described with respect to FIG. 1C above. As illustrated in FIG. 3D, an etching step, such as a reactive-ion etch, may be used to remove the excess membrane layer 331 from one side of the second substrate 340, leaving the of the second substrate 340.

Figure 3E:
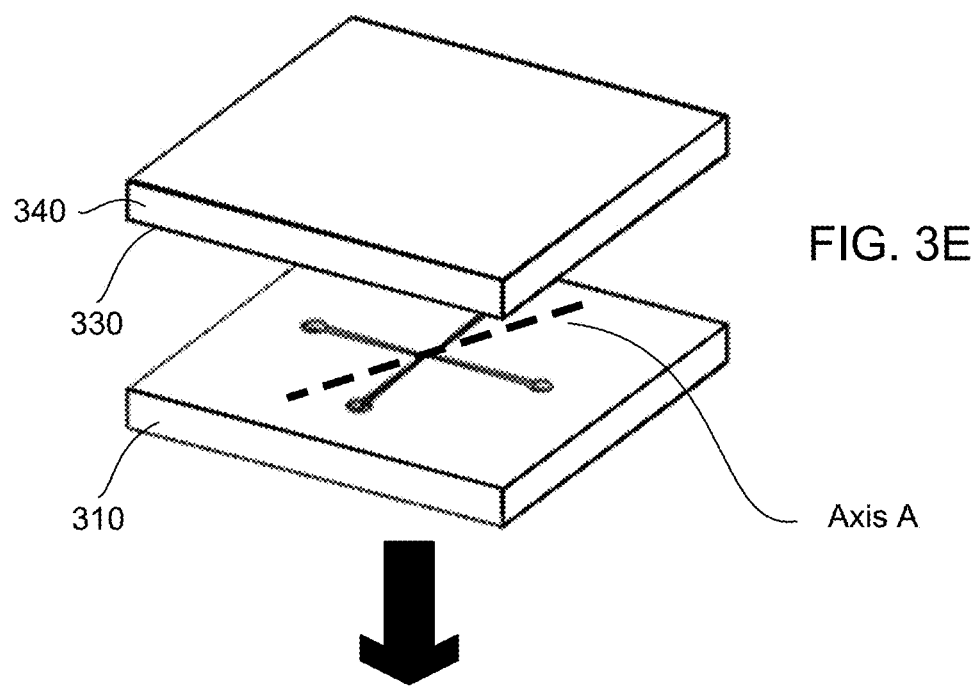
Figure 3F:
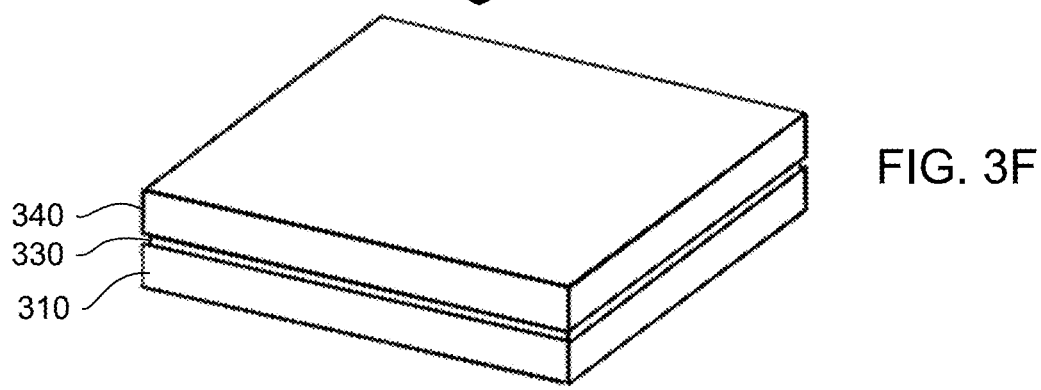
Figure 3G:
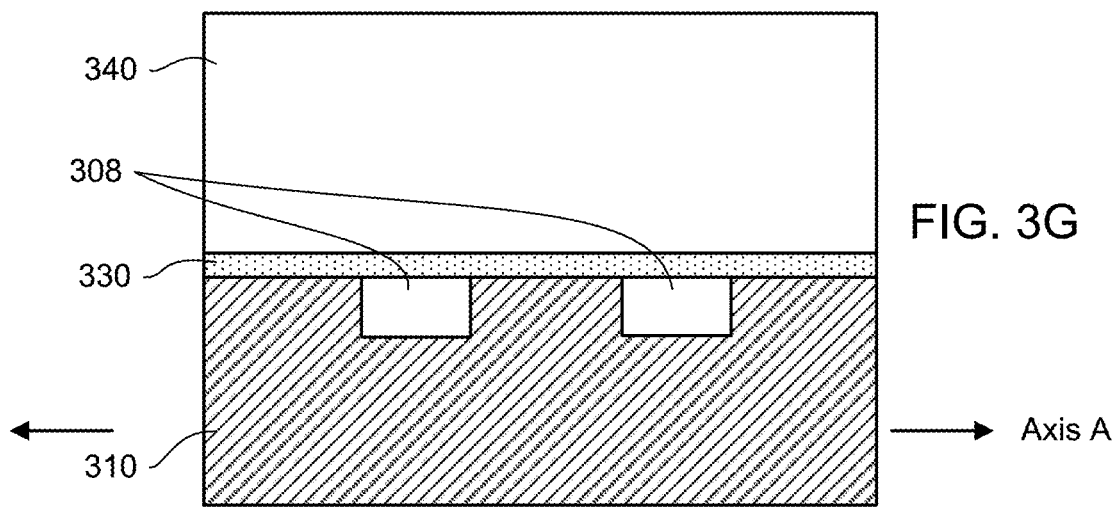

FIGS. 3E-3G illustrate steps for attaching the membrane layer 330 to the first insulating layer 310, according to one embodiment. As illustrated in FIG. 3E, the membrane layer 330 is positioned between the first 310 and second substrates 340 by positioning the first insulating layer 310 beneath the second substrate with the membrane layer 330 facing towards the first insulating layer 310. As illustrated in FIG. 3F, once assembled, the membrane layer 330 is located between the first insulating layer 310 and second substrate 340. One of a variety of bonding techniques is used to attach the membrane layer to the first insulating layer 310. In one embodiment, anodic bonding is performed at a temperature of 350 degrees Celsius, with a ramp up time of 40 minutes, a force of twenty Newtons, a voltage of 1000 Volts, waiting 5-10 minutes until the current drops to a few milli-Amperes and then stabilizes. In some embodiments, in addition to the bonding technique, compressive forces, such as mechanical forces, are applied to the first insulating layer 310 and the second substrate 340 to ensure a firm bonding between the membrane layer 330 and the first insulating layer 310.

FIG. 3G depicts a cross-sectional view of the bonded first insulating layer 310, membrane layer 330, and second substrate 340, according to one embodiment. Specifically, FIG. 3G depicts the cross section at Axis A, as shown in FIG. 3E. The second substrate 340 can then be removed using the techniques previously described in reference to FIG. 1E.

Although FIGS. 3E-3G demonstrate the process for attaching a membrane layer 330 to a first insulating layer 310 that is in accordance with the embodiments depicted in FIG. 1, as previously stated, this end product can also be achieved in accordance with the process depicted in FIG. 2. Namely, a sacrificial layer 250 can be located between the membrane layer 330 and the second substrate 340 such that the removal of the second substrate 340 can be achieved using the processes described in reference to FIG. 2C.

Figure 3H:
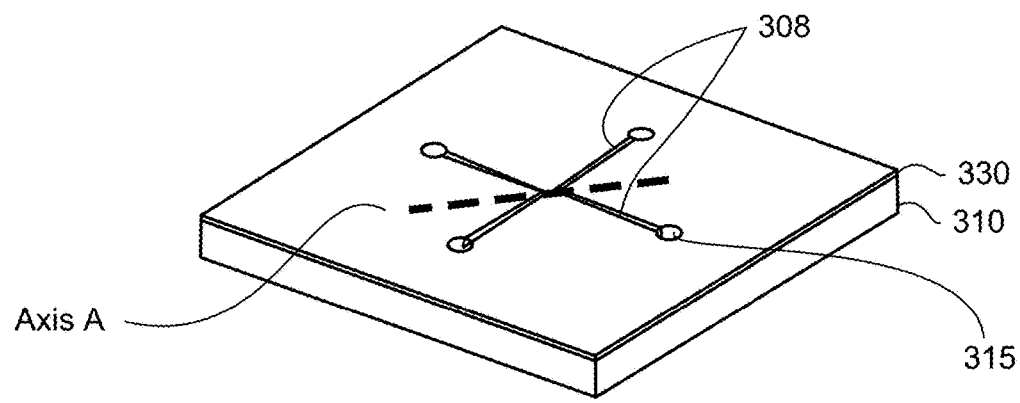
Figure 3I:
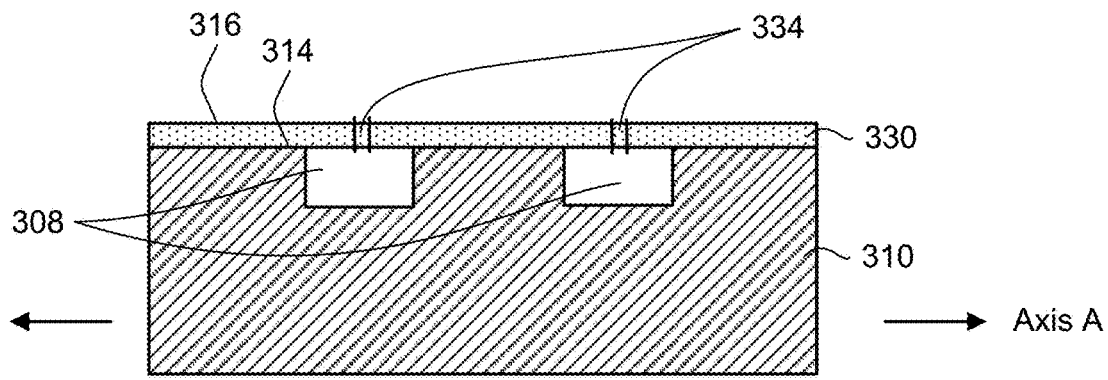

FIGS. 3H and 3I illustrate the nanopore device after removal of the second substrate 340, according to one embodiment. FIG. 3H illustrates a perspective view of the membrane layer 330 attached to the first insulating layer 310, and FIG. 3I illustrates a cross sectional view of the same that includes multiple nanopores 334 formed in the membrane layer 330. In various embodiments, as was described in reference to FIG. 1F, the membrane layer 330 can be thinned using mechanical or etching methods. Namely, the membrane layer 330 above the channels 308 can be thinned such that nanopores 334 can be more easily generated while also maintaining the structural integrity of the membrane layer 330.

Referring specifically now to the formation of the nanopores 334, the nanopores 334 penetrate from a top surface 316 of the membrane layer 330 to a bottom surface 314. In other words, the nanopore 334 serves to fluidically connect a top surface 316 of the membrane layer 330 to the bottom surface 314. The creation of the nanopore 334 can be achieved through a mechanical drilling process or through a beam etching process (e.g., RIE or Focus Ion Beam (FIB)), or by immersion lithography. Each nanopore 334 has an opening size that allows a small or large molecule, such as DNA, amino acids (proteins), and the like, to pass through. In one aspect, each pore is at least 1 nm in diameter. In some embodiments, each pore is at least 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, 90 nm or 100 nm in diameter. In some embodiments, the pore has a diameter that is between about 5 nm and about 200 nm. In some aspects, the pore has a substantially round shape. "Substantially round", as used here, refers to a shape that is at least about 80 or 90% in the form of a cylinder. In some embodiments, the pore is square, rectangular, triangular, oval, hexangular, or another polygon in shape.

In one embodiment, the nanopores 334 may be generated in the membrane layer 330 after the second substrate 340 is removed. In other embodiments, the nanopores 334 are generated in the membrane layer 330 prior to bonding the membrane layer 330 to the first insulating layer 310. As an example, the nanopores 334 may be generated in the membrane layer 330 while the membrane layer 330 was a part of the membrane assembly (e.g., membrane layer 330 coated onto the second substrate 340).

As depicted in FIG. 3I, each nanopore 334 is created in the membrane layer 330 to reside above a corresponding channel 308 in the first insulating layer 310. Therefore, each nanopore 334 enables the corresponding channel 308 to be fluidically connected to the space immediately above the nanopore 334. In the embodiment shown in FIG. 3I, Axis A represents the cross-section of the first insulating layer 310 where the channels 308 are closest in distance to one another. Here, the distance between the two nanopores 334 is between 1-10 μm. Two pore control can be exerted on DNA longer than 10 μm, for example, Lambda DNA is 16 μm. In other embodiments, the distance between the two nanopores 334 can be between 10-100 μm.

Figure 3J:
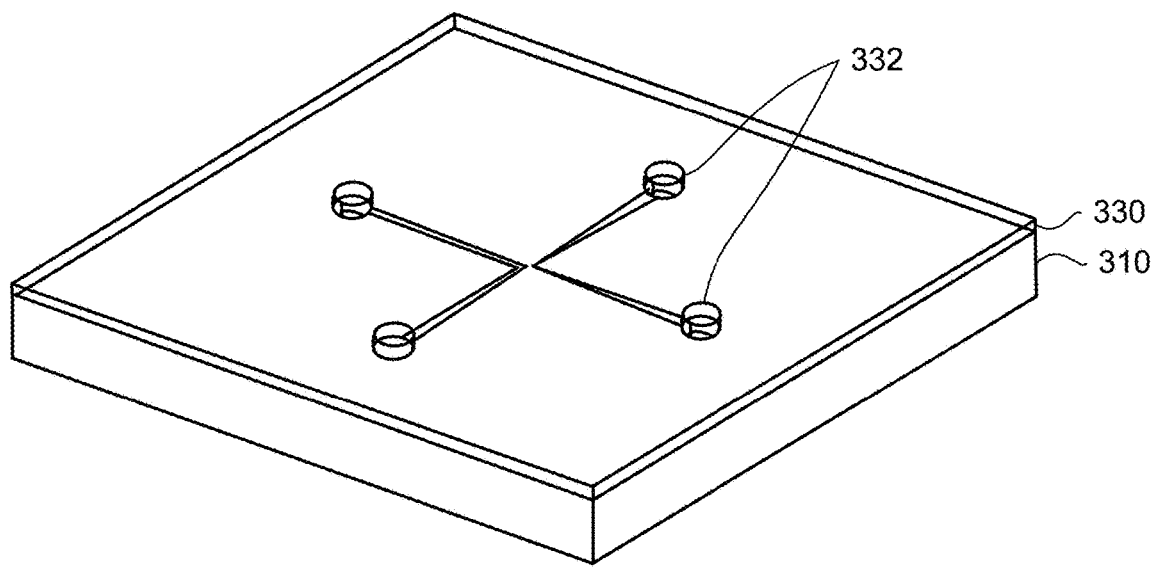

FIG. 3J is a perspective view of the first insulating layer 310 and bonded membrane layer 330 including holes 332 that penetrate through the membrane layer 330, according to one embodiment. As shown in FIG. 3J, four holes 332 are created. Each hole 332 is created in the membrane layer 330 such that the hole 334 is substantially aligned with a reservoir 315 that is located at the distal ends of the two channels 308. Thus, each hole 332 in the membrane layer 330 enables access to a reservoir 315 in the first insulating layer 310. The holes 332 can be broken open using a mechanical force by inserting a mechanical structure that penetrates the membrane layer 330. The amount of mechanical force used to open the holes is very low, as the membrane layer 330 itself is very thin. In some embodiments, the membrane layer 330 is thinned down where the holes 332 are to be mechanically created. In one embodiment, the holes are approximately 500 μm, and thus are similar in size to the reservoirs.

Figure 3L:
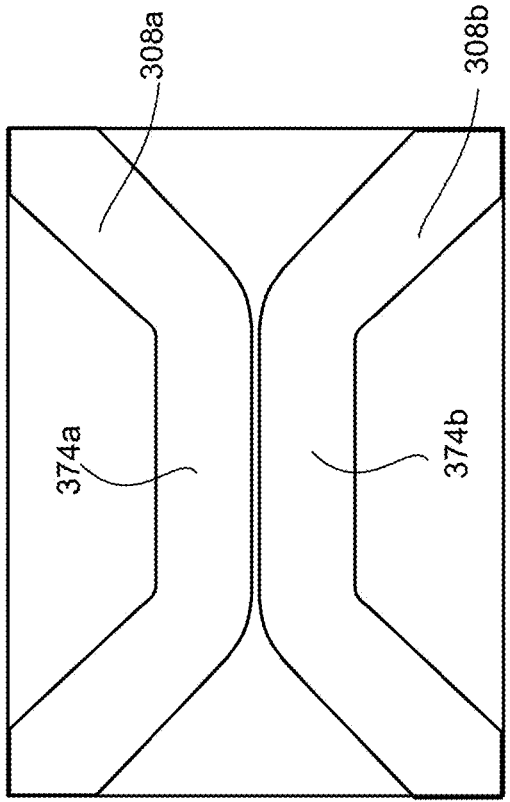
Figure 3M:
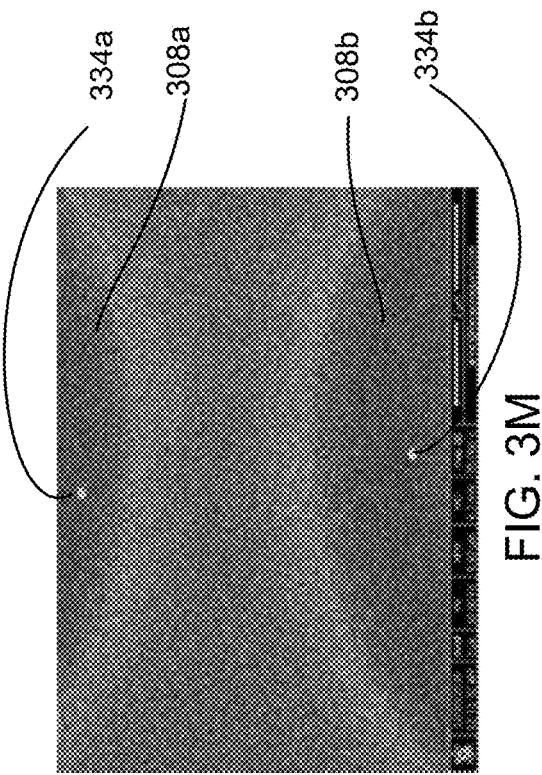
Figure 3K:
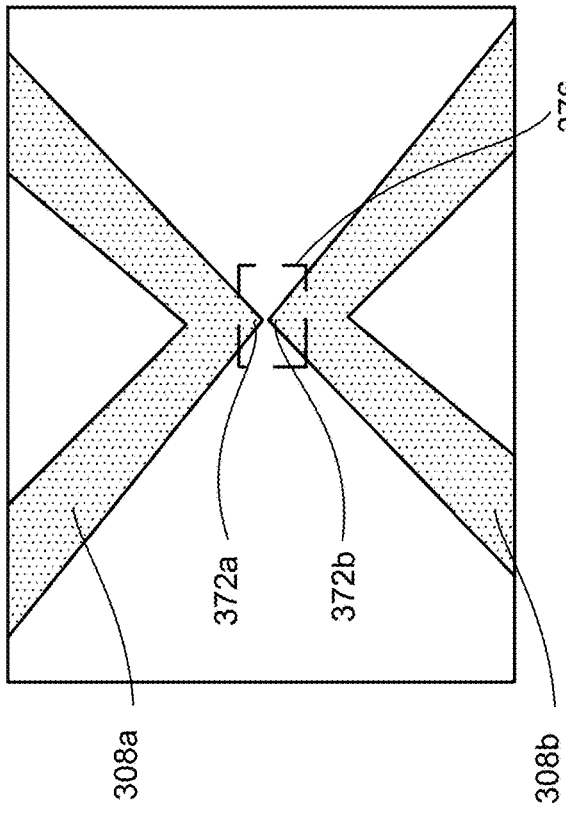

FIG. 3K and FIG. 3L each depict a top-down view of the membrane layer 330 bonded to the first insulating layer 310 that includes the point where the channels 308 of the first insulating layer 310 are closest to one another, in accordance with an embodiment. More specifically, as shown in FIG. 3K, the channels 308 are formed so as to nearly cross, but not intersect, each other along each channel 308. In one embodiment, at the point where the first channel 308a and second channel 308b are closest to one another on the first insulating layer 310, each of the first channel 308a and the second channel 308b form an elbow point 372a and 372b. In other words, the first channel 308a and the second channel 308b each converge to their respective elbow point 372 location. In some embodiments, the elbow point 372 of each channel 308 is also the midpoint of each channel.

FIG. 3L depicts a different embodiment which includes a different orientation of the first channel 308a and second channel 308b on the first insulating layer 310. More specifically, the closest distance between the first channel 308a and second channel 308b corresponds to an extended portion 374a of the first channel 308a and an extended portion 374b of the second channel 308b. As shown in FIG. 3L, the extended portion 374a of the first channel 308a is parallel to the extended portion 374b of the second channel 308b.

FIG. 3M illustrates an example image depicting a electron microscope view of the nanopores 334 and the channels 308. For example, FIG. 3M can depict the blown up inset 376 as indicated in FIG. 3K. As described above, nanopores 334 can be generated in the membrane layer 330 above the channels 308. As shown in FIG. 3M, a first nanopore 334a is located above the first channel 308a and a second nanopore 334b is located above the second channel 308b. In various embodiments, the nanopores 334 are generated in the membrane layer 330 above the location where the channels 308 are closest to one another. In this example image, the distance between the first nanopore 334a and the second nanopore 334b is about 3.5 µm. However, as described above, in other embodiments, the distance between first 334a and second nanopore 334b can be between 1-10 µm or even between 10-100 µm.

Figure 3N:
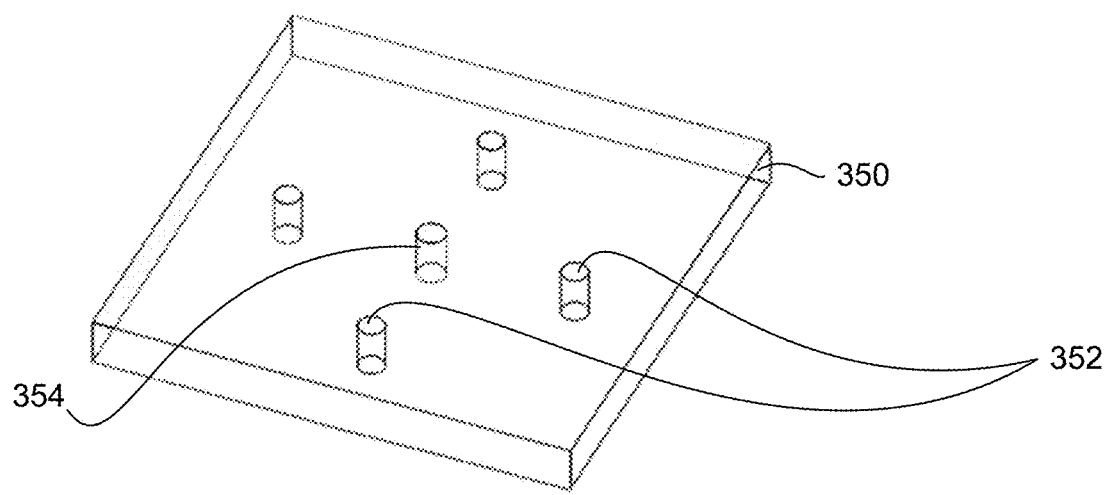

FIG. 3N is a perspective view of a cover 350 for the nanopore device, according to one embodiment. The cover 350 is made of an insulating material, examples of which include glass and polydimethylsiloxane (PDMS). In one embodiment, the cover 350 is between 200 µm to 1 mm in thickness. As shown in FIG. 3N, the cover 350 includes five distinct holes each of which fully penetrates through the thickness of the cover 350. Of the five distinct holes, one is a center hole 354 that is located in the cover 350 so as to be situated directly above the nanopores 334 in the membrane layer 330 when the cover 350 is attached the membrane layer 330. The remaining four holes 352 are located so as to be substantially aligned with the holes 332 of the membrane layer 330, again once the cover 350 is attached to the membrane layer 330. In other words, access to a reservoir 315 in the first insulating layer 310 is provided through a hole 332 of a membrane layer and a hole 352 in the cover. The four holes 352 in the cover 350 are similarly sized to those in the membrane layer 330 and the reservoirs 315 in the first insulating layer 310. Each of the center hole 354 and four holes 352 in the cover 350 may be generated through a variety of techniques, one example of which is drilling using an appropriately sized drill bit.

Figure 3O:
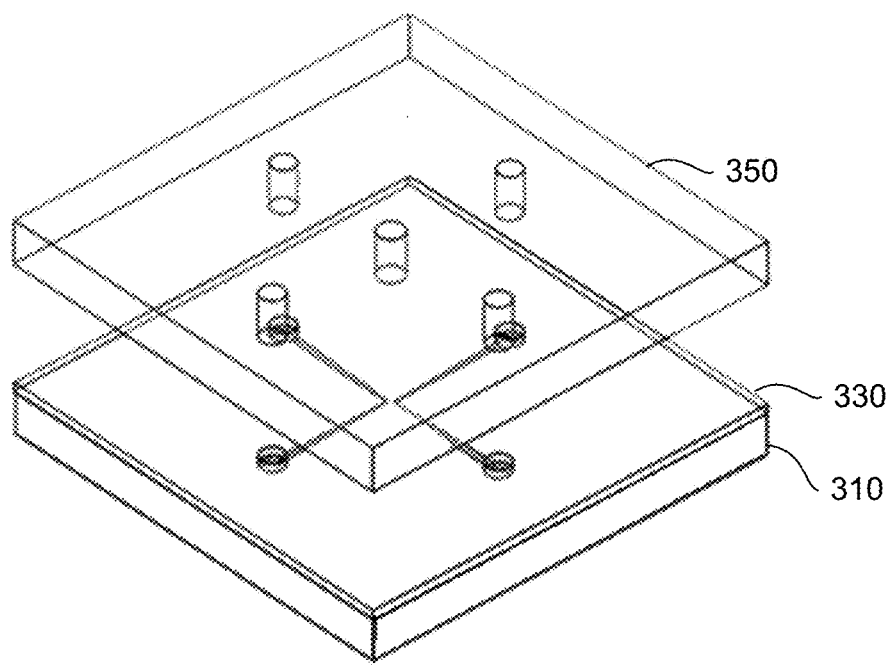

FIG. 3O illustrates the bonding of the cover 350 to the membrane layer 330, according to one embodiment. As previously described and currently illustrated in FIG. 3O, the cover 350 is positioned over the membrane layer 330 such that the holes 352 in the cover 350 substantially align with the holes 332 in the membrane layer 330. The cover 350 may be bonded to the membrane layer 330 using a variety of techniques, including any of the techniques that were described above in bonding the first insulating layer 110 and the membrane 130 (as described in reference to FIG. 1D). For example, the cover 350 is attached to the membrane layer 330 using plasma bonding if the cover is made by PDMS or anodic bonding if the cover is made of glass. Compressive forces may be applied to the cover 350 and the first insulating layer 310 to ensure that a complete bond is achieved.

Figure 3P:
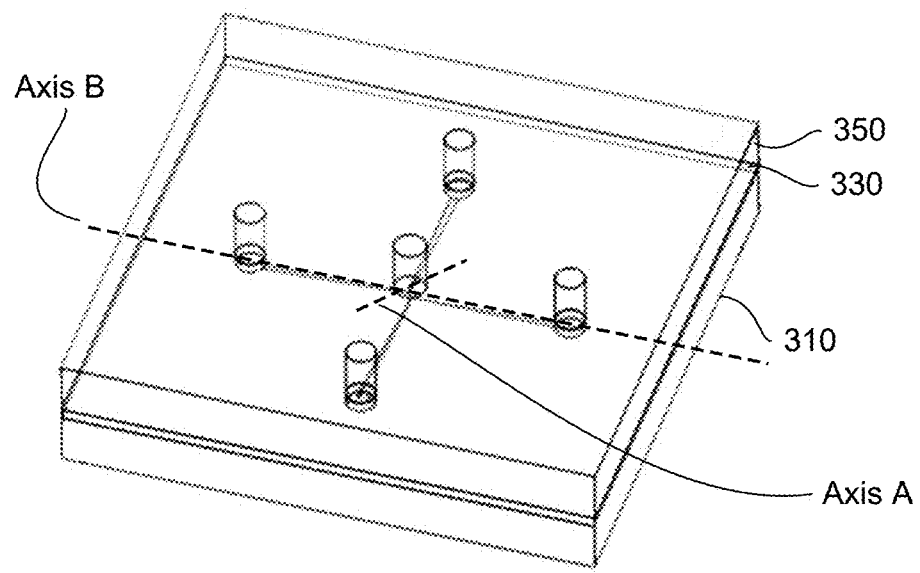

FIG. 3P depicts a perspective view of the fully assembled nanopore device 300. Specifically, the nanopore device 300 includes the first insulating layer 310 in contact with the membrane layer 330 which is further in contact with the cover 350.

Figure 3Q:
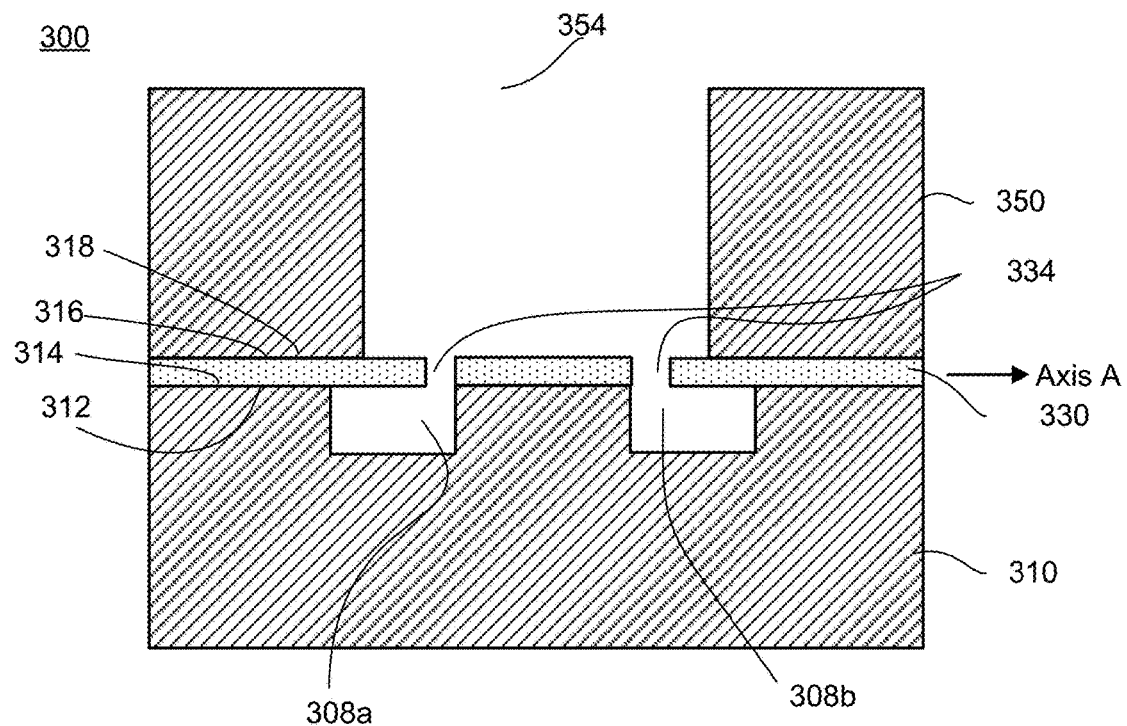

FIG. 3Q illustrates a first cross sectional view of the nanopore device 300 along axis A as indicated in FIG. 3P, according to one embodiment. Axis A depicts the cross-sectional view where the two channels 308 of the first insulating layer 310 are closest to each other in distance. More specifically, FIG. 3Q illustrates the two nanopores 334 in the membrane layer 330 and their relative positions above the underlying channels 308 in the first insulating layer 310. Additionally, the center hole 354 of the cover 350 is aligned above nanopores 334. Altogether, each nanopore 334 of the membrane layer 330 fluidically connects a corresponding channel 308 of the first insulating layer 310 to the center hole 354 of the cover.

Altogether, the nanopore device 300 contains multiple layers. Specifically, the first insulating layer 310 is bonded to the membrane layer 330 through a surface 312 of the first insulating layer 310 and a first surface 314 of the membrane layer 330. A second surface 316 of the membrane layer 330 is bonded to a surface 318 of the cover 350.

Figure 3R:
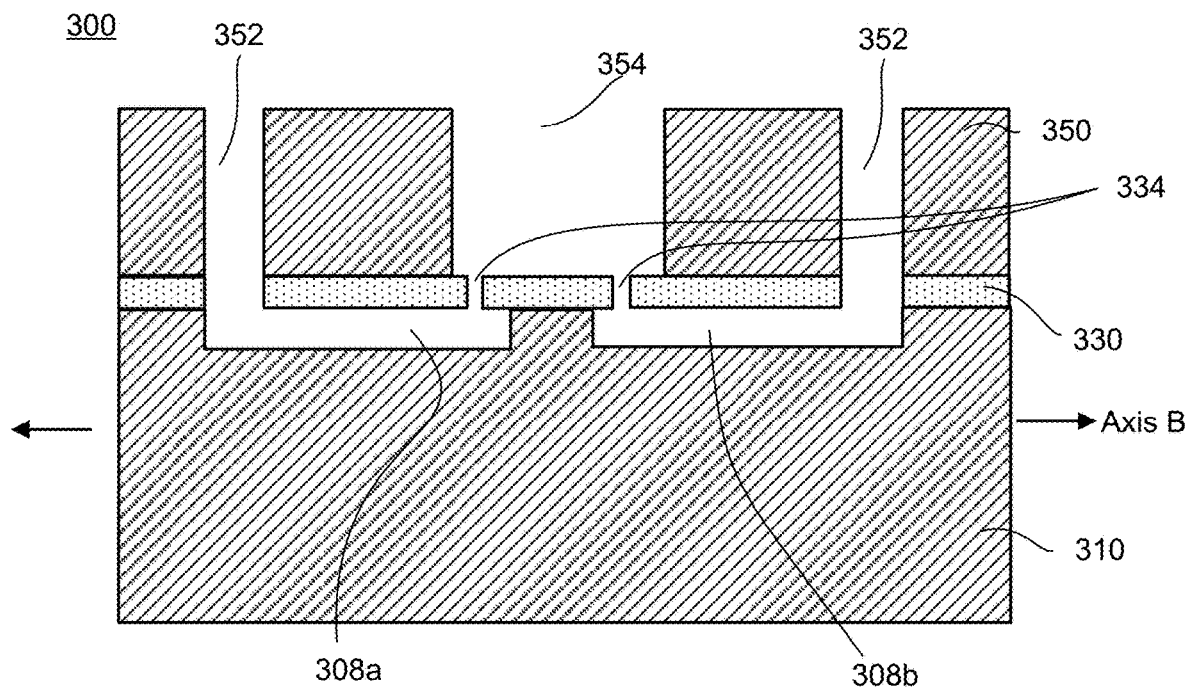

FIG. 3R illustrates a second cross sectional view of the nanopore device 300 along axis B as marked in FIG. 3P, according to one embodiment. Specifically, Axis B depicts the cross-section of the nanopore device 300 along a portion of the first channel 308a and a portion of the second channel 308b. Further depicted in FIG. 3R is the fluid connection of each channel 308 (e.g., reservoir in the distal end of the channel 308) to a hole 352 in the cover 350 of the nanopore device 300.

Note that although this section discusses a dual pore device, a single pore device is also contemplated (not illustrated). Such a device would include only a single channel, and only three holes in the membrane layer that correspond to three holes in the cover. As an example, the single channel may be linearly designed. Therefore, the three holes of the membrane layer are collinear with two of the holes each located over a reservoir at each end of the single channel.

IV. EXAMPLE TWO CHANNEL/DUAL MEMBRANE DEVICE

A variant of the process described in Section III above may be used to produce a nanopore device that includes two channels in different planes that may be used for dual nanopore sensing and control.

Figure 4A:
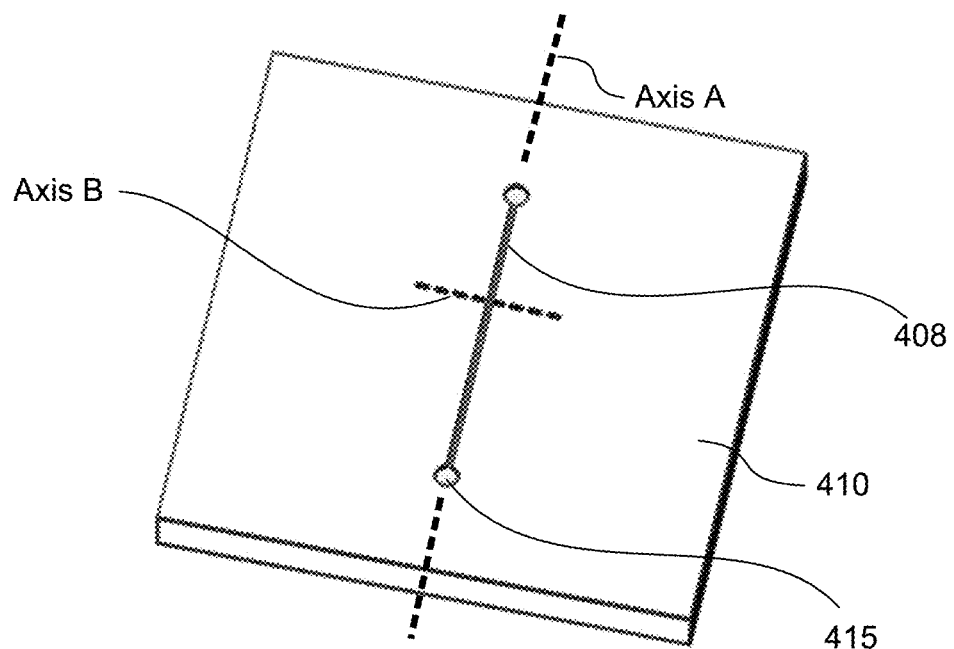
FIGS. 4A-4U illustrate a method for forming a nanopore device that includes two channels in two different planes that may be used for dual nanopore sensing and control, according to one embodiment.
Figure 4B:
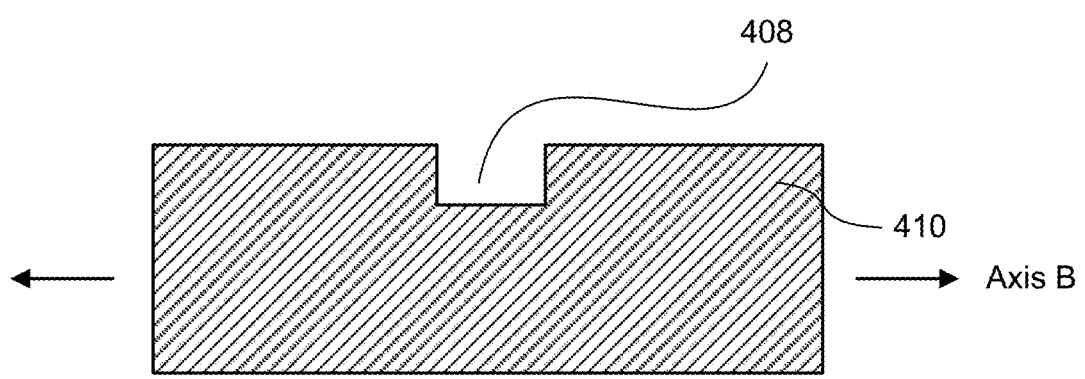
Figure 4C:
Figure 4D:
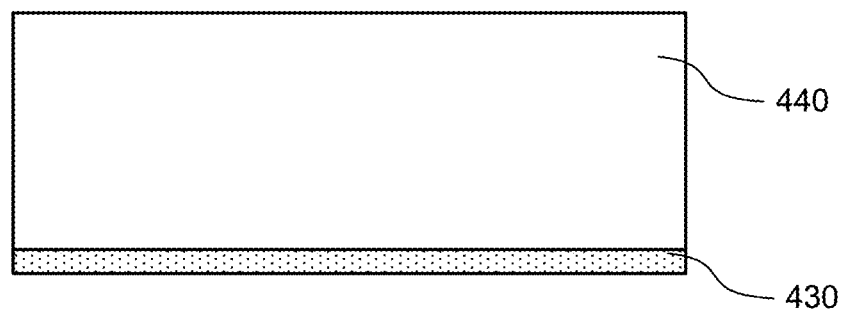

FIGS. 4A-B illustrate a first insulating layer 410 from a perspective and cross sectional view along the axis A of FIG. 4A, respectively, according to one embodiment. The first insulating layer 410 includes a single channel 408 with reservoirs 415 located at the distal ends of the channel 408.

The portion of the channel 408 between the reservoirs 415 possesses either a constant width, or possesses a width that tapers as it approaches the midpoint along the channel length.

Figure 4E:
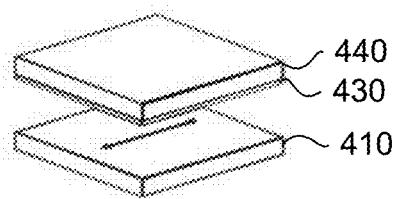
Figure 4F:
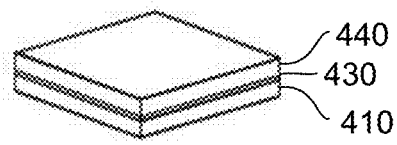
Figure 4G:
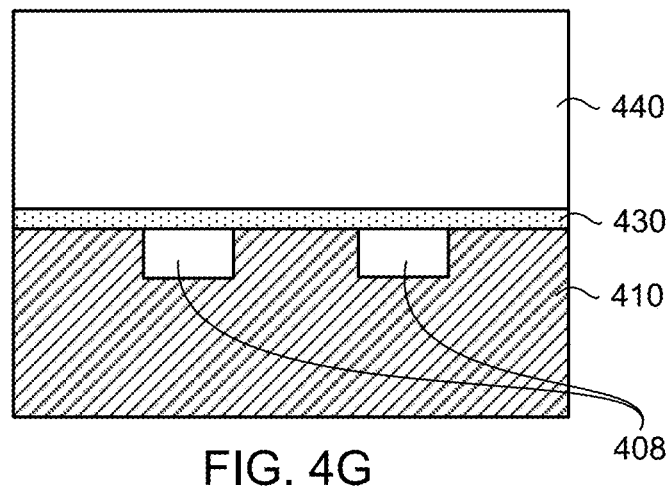

FIGS. 4C-4G illustrate the process for generating a membrane assembly that includes bonding a membrane layer 430 to the first insulating layer 410, according to one embodiment. The membrane layer 430 is formed on a second substrate 440 as described with respect to FIGS. 1C, 3C, and 3D above. As shown in FIG. 4E-4G, the membrane layer 430 is bonded to the first insulating layer 410 as described above with respect to FIGS. 1D and 3E-3G. In other embodiments, the membrane assembly includes the first insulating layer 410, membrane layer 430 and a sacrificial layer located between the first insulating layer 410 and membrane layer 430, as described with respect to FIG. 2A.

The membrane assembly is attached to the first insulating layer 410. For example, the first membrane layer 430 is bonded to the first insulating layer 410 on the surface where the channel 408 is located using any of the techniques previously described in reference to FIG. 1D. The second substrate 440 can then be removed using the techniques described in reference to FIG. 1E or 2C.

Figure 4H:
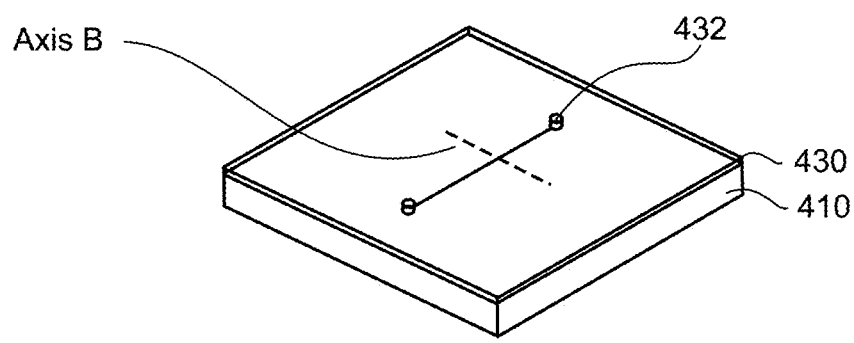

FIG. 4H is a perspective view of the first insulating layer 410 bonded to the membrane layer 430 that includes holes 432 that penetrate through the first membrane layer 430, according to one embodiment. Each hole 432 in the first membrane layer 430 is located to be substantially aligned with each reservoir 415 located at each end of each of the two channels 408. The holes can be broken open using a mechanical force. The amount of mechanical force used to open the holes is very low, as the membrane itself is very thin (as above, somewhere between 10-100 nm).

Figure 4I:
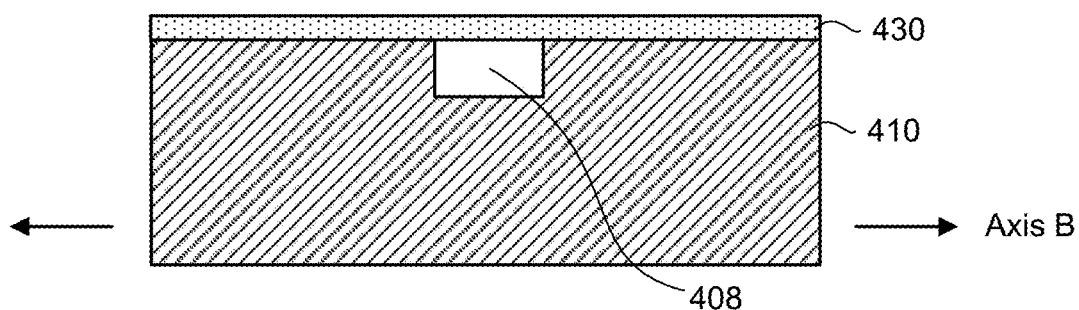

FIG. 4I is a side view along axis B as indicated in FIG. 4H. Here, the first membrane layer 430 is positioned above the first insulating layer 410. In various embodiments, the first membrane layer 430 may be thinned in a portion that is located above the channel 408.

Figure 4J:
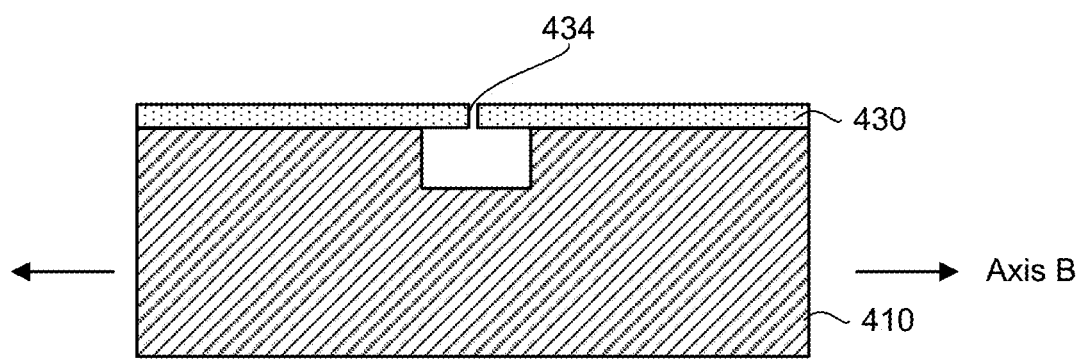

FIG. 4J is a cross sectional view of the nanopore device once a nanopore 434 has been created in the first membrane layer 430. The nanopore 434 enables the underlying channel 408 to be fluidically connected to the space above the nanopore 434. The nanopore 434 can be created using the methods described previously in reference to FIGS. 3H and 3I.

Figure 4K:
Figure 4L:
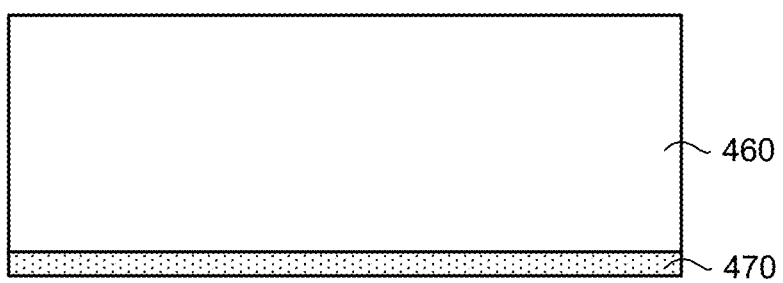

FIGS. 4K and 4L illustrate a second membrane assembly that facilitates the bonding of a second membrane layer 470. More specifically, FIGS. 4K and 4L depict cross sectional views of processing of a second substrate 460, according to one embodiment. In such a dual membrane device, a second membrane layer 470 is bonded to the nanopore device after the holes 432 and nanopore 434 have been created in the first membrane layer 430. The second membrane layer 470 is attached to the second substrate 460 in the same manner as described with respect to FIGS. 4C and 4D.

Figure 4M:
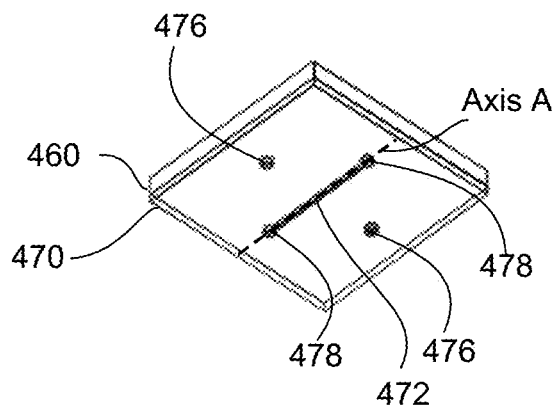
Figure 4N:
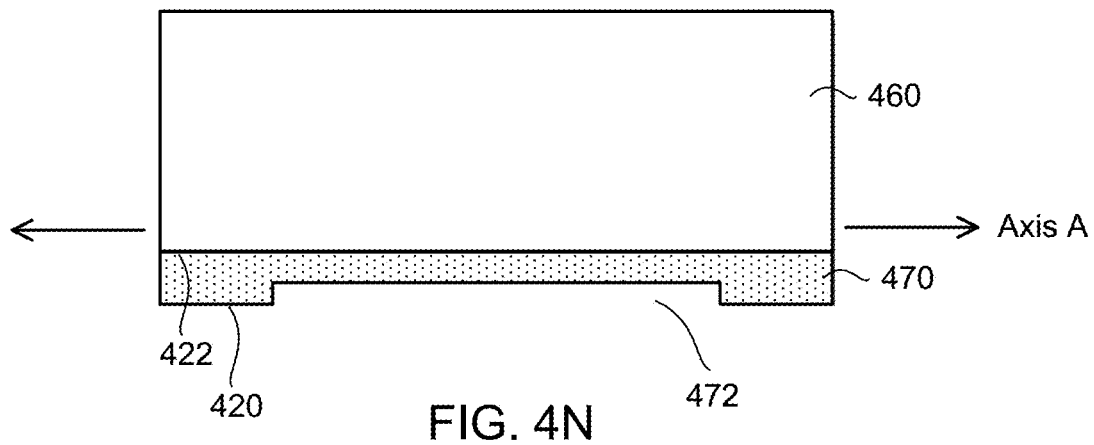
Figure 4O:
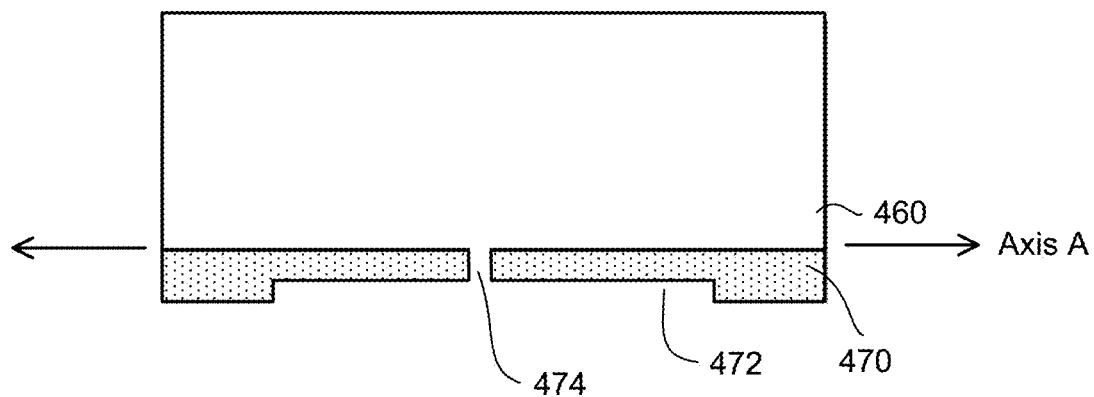

FIGS. 4M-4O illustrate etching of a membrane channel 472 of the second membrane layer 470, according to one embodiment. FIG. 4M illustrates a perspective view where the membrane channel 472 is formed along Axis A in the second membrane layer 470. FIG. 4N illustrates a cross sectional view of the membrane channel 472 along Axis A. The etching of the membrane channel 472 occurs on a first surface 420 of the second membrane layer 470 while the second surface 422 of the second membrane layer 470 is in contact with the second substrate 460. In one embodiment, the membrane channel 472 is 5 µm wide and 3 mm long. In some embodiments, the depth of the membrane channel 472 is approximately half of the thickness of the second membrane layer 470 which may be between 100-500 µm in thickness. In one embodiment, this membrane channel 472 in the second membrane layer 470 is formed using an etch process, however other techniques may also be used.

Referring back to FIG. 4M, the second membrane layer 470 may also include holes 476 and 478 that penetrate through the second membrane layer 470. Each hole 476 or 478 is mechanically generated or etched. As shown in FIG. 4M, two holes 478 are located at the either ends of the membrane channel 472. The second membrane layer 470 also includes two holes 476 that are each located to substantially align with a reservoir 415 in the first insulating layer 410 and a hole 432 in the first membrane layer 430.

FIG. 4O illustrates the second membrane layer 470 including a nanopore 474 in the center of the membrane channel 472, according to one embodiment. The pore may be formed using mechanical drilling, or using another similar technique as described in reference to FIGS. 3H and 3I.

Figure 4P:
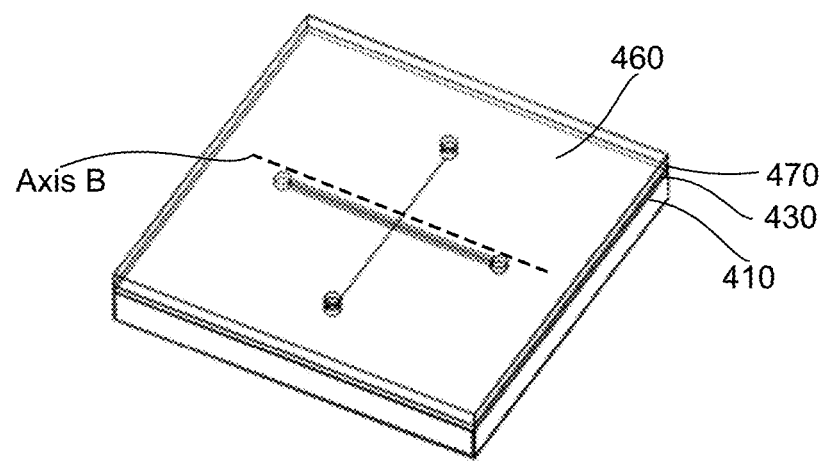
Figure 4Q:
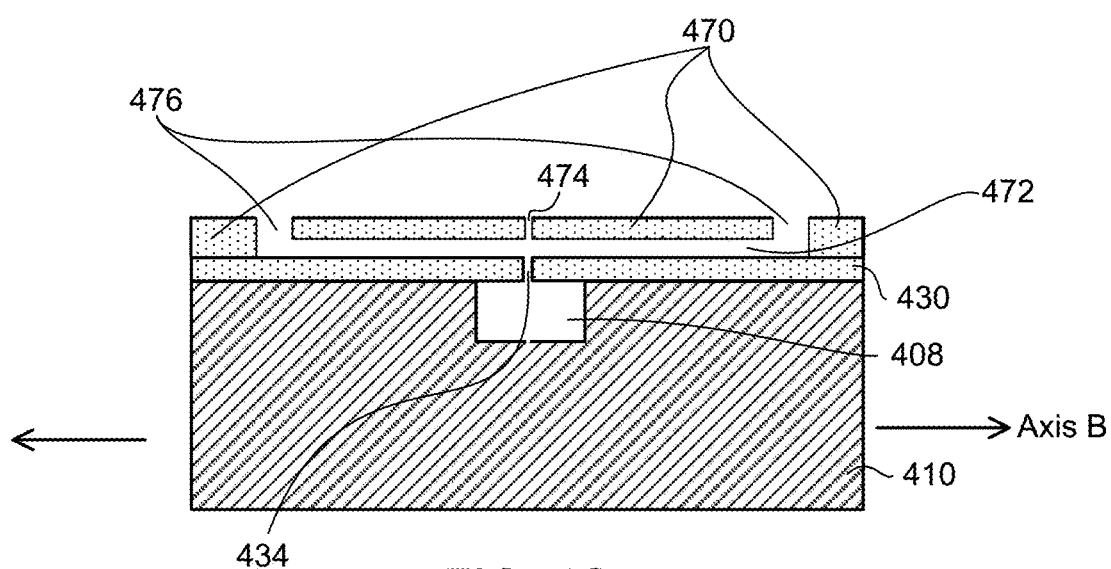

FIGS. 4P and 4Q illustrate the attachment of the second membrane layer 470 to the first membrane layer 430, according to one embodiment. FIG. 4P is a perspective view which illustrates that the second membrane 470 is attached to the first membrane layer 430 such that the membrane channel 472 is oriented at a 90 degree angle (orthogonal to) the first channel 408 in the first insulating layer 410. The membrane channel 472 and the first channel 408 in the first insulating layer 430 are further positioned so as to cross near or at each other's midpoints.

FIG. 4Q illustrates a cross sectional view of the first insulating layer 410, first membrane layer 430, and second membrane layer 470 along Axis B, according to one embodiment. The second membrane layer 470 is bonded to the first membrane layer 430 using any of the processes described with respect to FIGS. 1C-1D in section IV above, with the second membrane layer 470 attaching to the first membrane layer 430 (instead of the membrane layer attaching to the first insulating layer). At the end of those processes, the second substrate 460 is removed using the techniques described above in reference to FIG. 1E or 2C. Note that, although FIG. 4Q only depicts a small portion of the second membrane layer 470 that contacts the first membrane layer 430, the membrane channel 472 covers only a relatively small portion of the surface area of the second membrane layer 470, and much of the remainder of the surface area of the second membrane layer 470 is in direct contact with the first membrane layer 430.

In another embodiment, rather than forming the nanopore 474 in the second membrane layer 470 separately from the forming of the nanopore 434 in the first membrane layer 430, both nanopores may be formed together at this step in the process (i.e., after bonding of the first 430 and second membrane layers 470 and after the second substrate 460 has been removed).

Figure 4R:
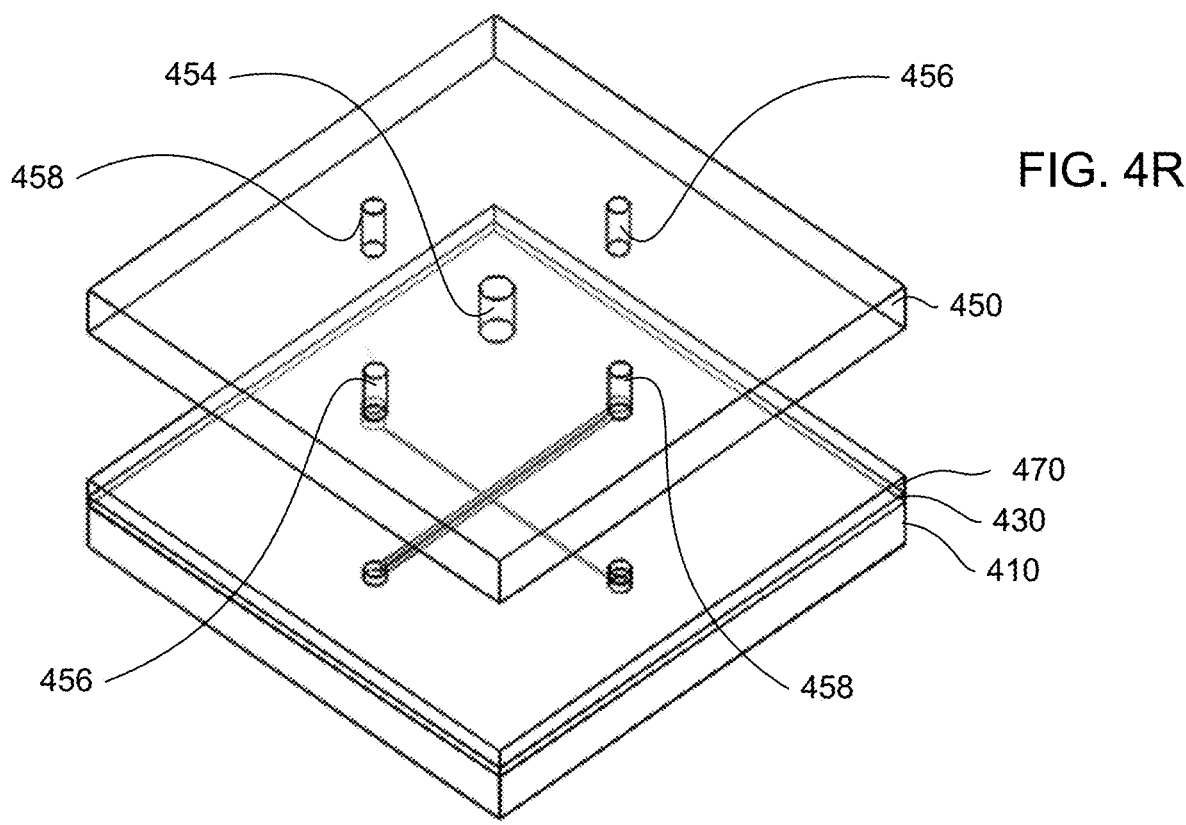
Figure 4S:
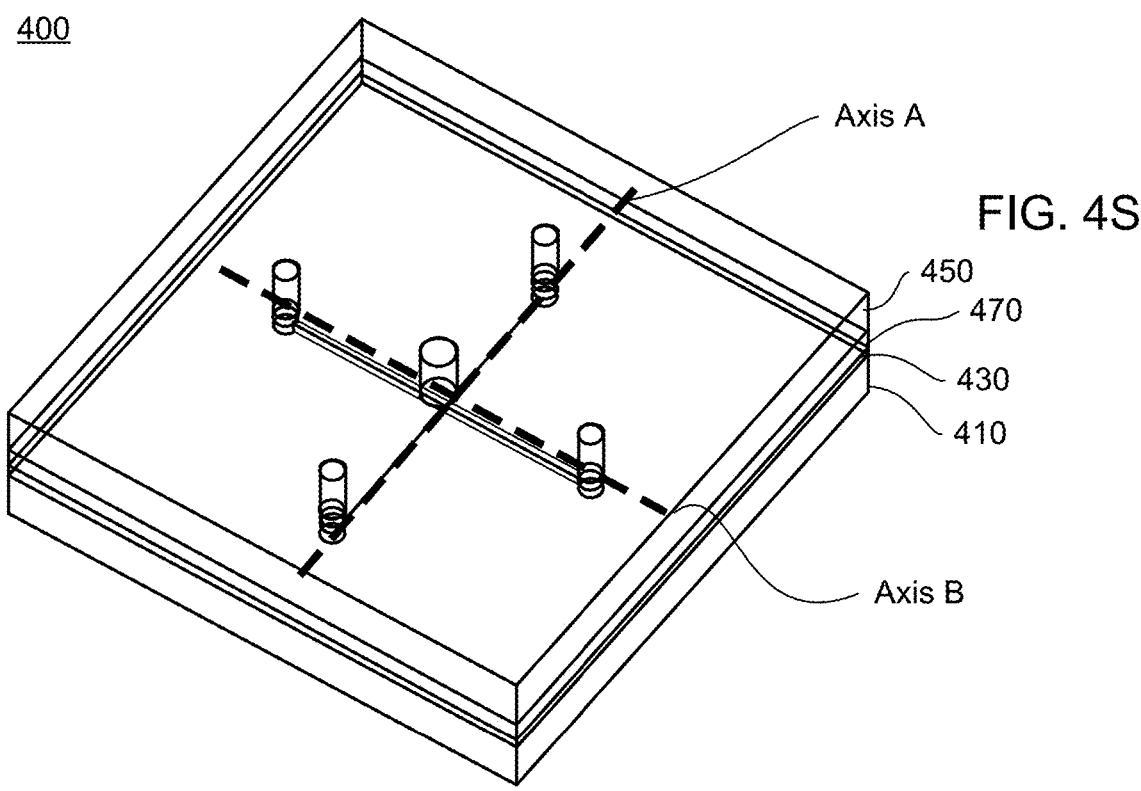

FIGS. 4R and 4S illustrate attaching a cover 450 to the nanopore device, according to one embodiment. As described above, the cover 450 is made of an insulating material, and has multiple holes 452 and 454. For example, the cover 450 may include a center hole 454 and four outer holes 452. Two of the outer holes 456 are positioned in the cover 450 to substantially align with the reservoirs 415 that are located at the distal ends of the channels 408 in the first membrane layer 410, and the other two outer holes 458 are positioned to substantially align with the holes 478 in the second membrane layer 470. FIG. 4S depicts the cover 450 bonded to the second membrane layer 470, according to one embodiment. The cover 450 is placed in contact with the second membrane layer 470, and bonded, for example as described above with respect to FIG. 3M.

Figure 4T:
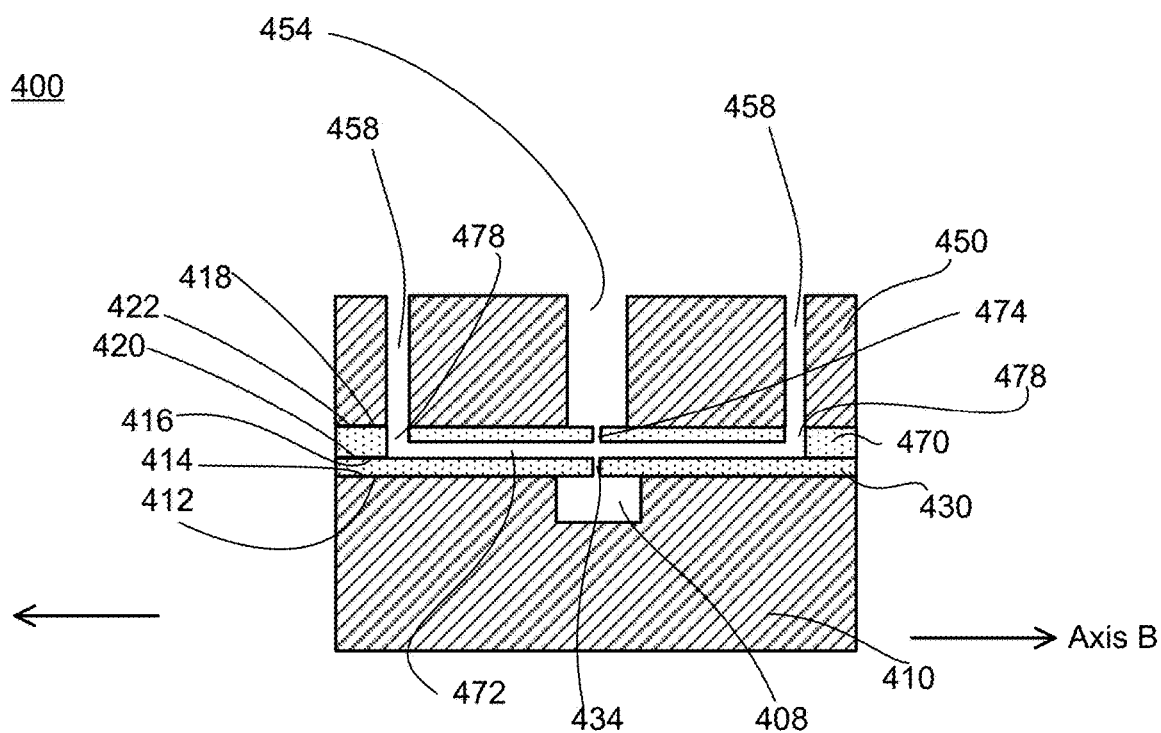
Figure 4U:
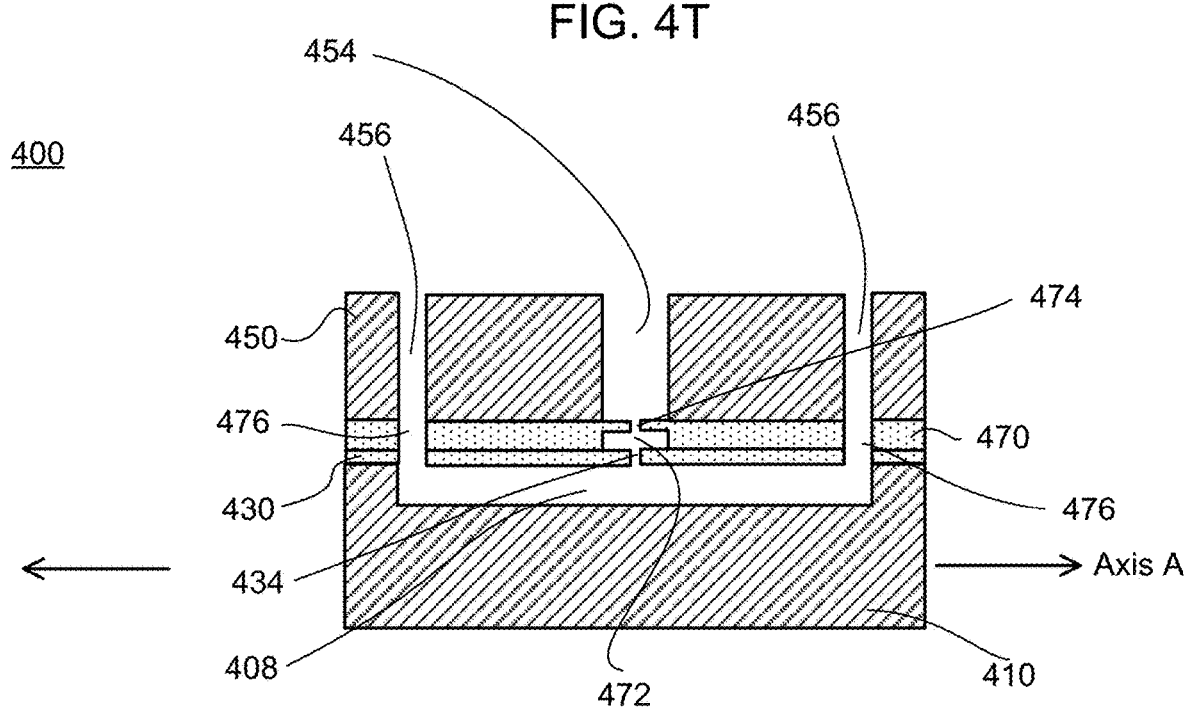

FIG. 4T-4U illustrate two different cross sectional views of the dual membrane nanopore device 400, according to one embodiment. FIG. 4T illustrates a cross section along the Axis B, and FIG. 4U illustrates a cross section along Axis A. The nanopore device 400 is composed of multiple layers. Specifically, the first insulating layer 410 is bonded to the first membrane layer 430 through the surface 412 of the first insulating layer 410 and the first surface 414 of the first membrane layer 430. The first membrane layer 430 is further bonded to the second membrane layer 470. Here, the second surface 416 of the first membrane layer 430 forms the bond with the first surface 420 of the second membrane layer 470. The second membrane layer 470 is further bonded to the cover 450. Specifically, the second surface 422 of the second membrane layer 470 is bonded to the surface 418 of the cover 450.

In both cross-sectional views, the nanopore 434 of the first membrane layer 430 and the nanopore 474 of the second membrane layer 470 are substantially aligned with one another and the center hole 454 of the cover 450. Therefore, the nanopore 434 in the first membrane layer 430 fluidically connects the channel 408 of the first insulating layer 410 to the membrane channel 472 of the second membrane layer 470. The nanopore 474 of the second membrane layer 470 fluidically connects the membrane channel 472 of the second membrane layer 470 to the center hole 450 of the cover 450.

FIG. 4T specifically depicts the outer holes 458 of the cover 450 that are substantially aligned to the holes 478 of the second membrane layer 470. As such, the membrane channel 472 is in fluidic connection with the outer holes 458 of the cover. FIG. 4U specifically depicts outer holes 456 of the cover 450 that are substantially aligned to the holes 476 of the second membrane layer that are in fluidic connection with the channel 408 of the first insulating layer 410. More specifically, the outer holes 456 of the cover substantially align with the reservoirs 415 (shown in FIG. 4A) of the first insulating layer 410. Each pair of holes 476 and 478, each associated with a different one of the channels (408 or 472), permits isolated electrical access to each nanopore (434 and 474) separately, with the membrane channel 472 acting as a ground electrode for dual-pore sensing and control.

V. MULTI-PORE ARRAY DEVICE

A variant of the processes described in Section I-IV above may be used to produce a nanopore array device that includes many separate multi-nanopore devices using a common first insulating layer.

Figure 5A:
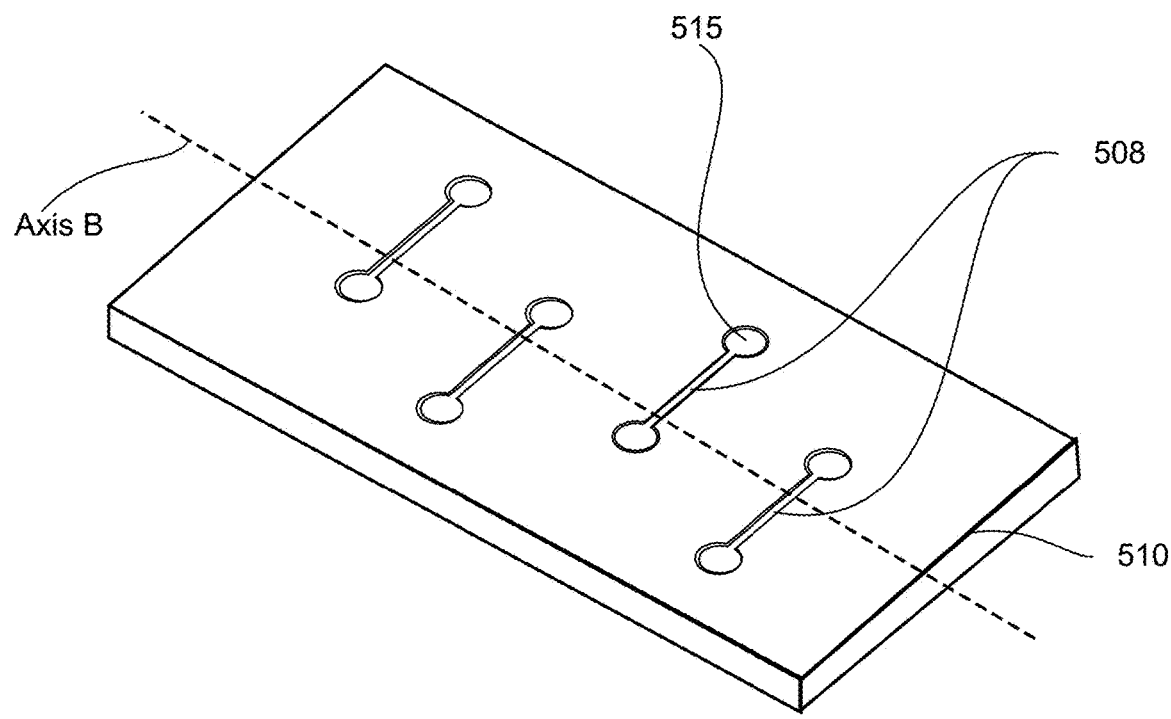
FIGS. 5A-5I illustrate a method for forming a nanopore array device that includes separate multi-nanopore channels using a common first insulating layer, according to one embodiment.
Figure 5B:
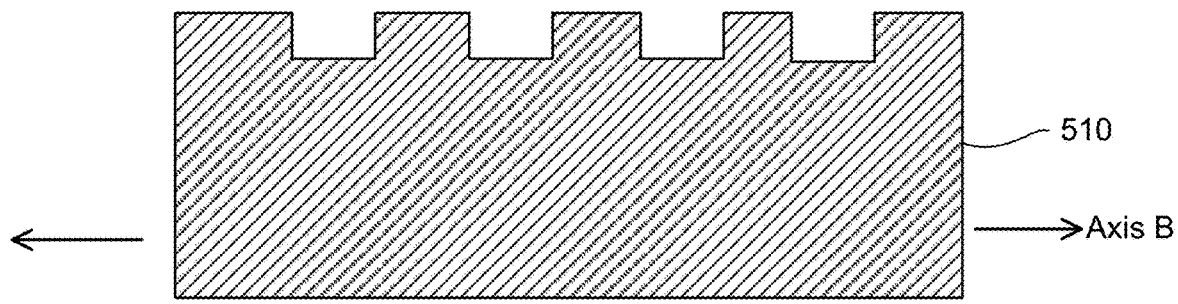

FIG. 5A-5B illustrate a perspective view and a cross sectional view, respectively, of a first insulating layer 510 including a number of channels 508 all oriented parallel to each other. Specifically, FIG. 5B depicts a cross sectional view along axis B as indicated in FIG. 5A. The channels 508 are similar to those described with respect to FIG. 1 above. Each channel 508 includes two reservoirs 515, each located on the distal ends of each channel 508. In various embodiments, the channels 508 need not be offset from one another as depicted in FIG. 5A.

Figure 5C:
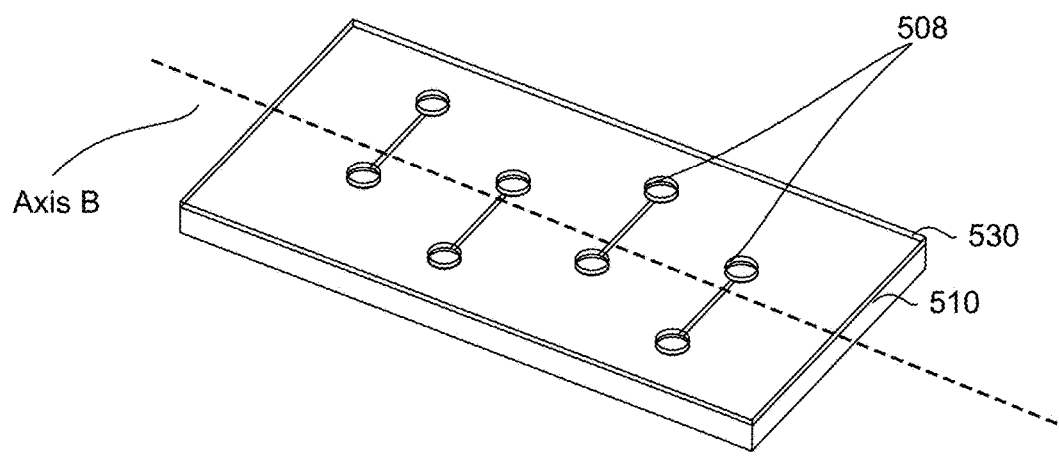
Figure 5D:
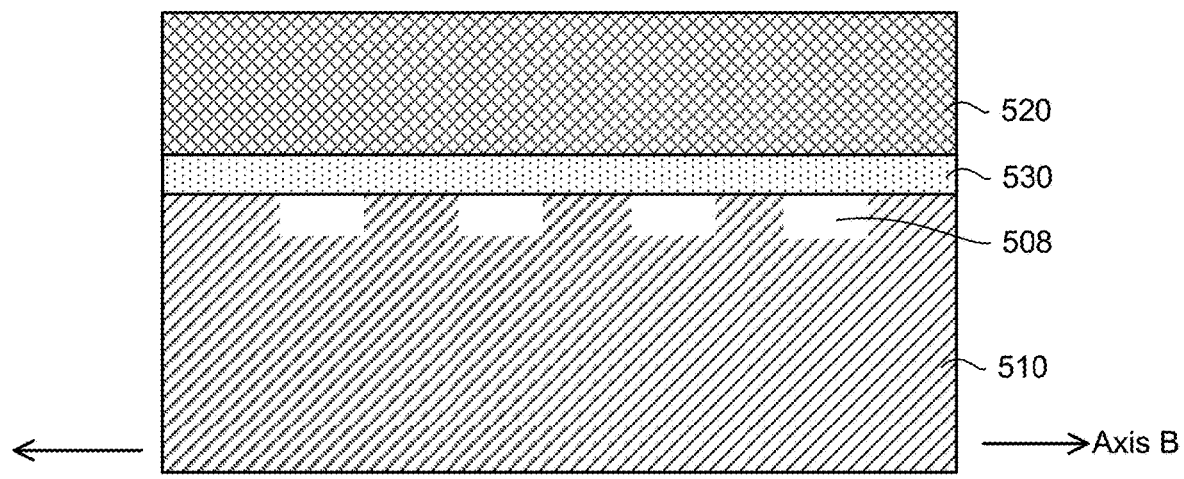
Figure 5E:
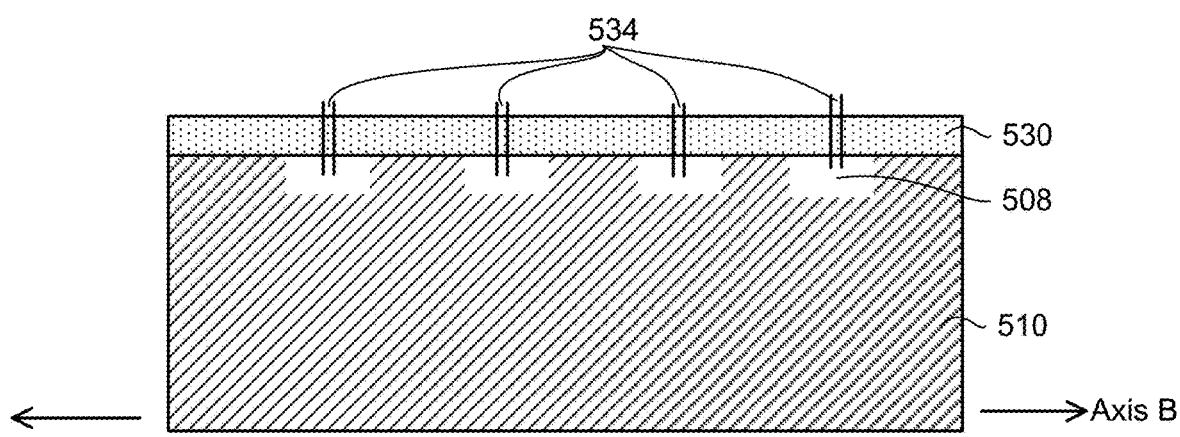

FIGS. 5C-5E illustrate a process for bonding a membrane layer 530 to the first insulating layer 510 including multiple channels 508, according to one embodiment. Regarding FIGS. 5C and 5D, the processes used to bond the membrane layer 530 to the first insulating layer is the same as described with respect to FIGS. 1B-1E. For example, a membrane assembly (including second substrate 520 and membrane layer 530) can be bonded to the first insulating layer 510 through the membrane layer 530 and subsequently, the second substrate 520 is removed. As illustrated in FIG. 5E, after the second substrate 520 has been removed, nanopores 534 are generated in the membrane layer 530. Each nanopore 534 in the membrane layer 530 corresponds to a channel 508 in the first insulating layer 510. As above, the nanopores 534 can be created using a mechanical force or etching process.

Figure 5F:
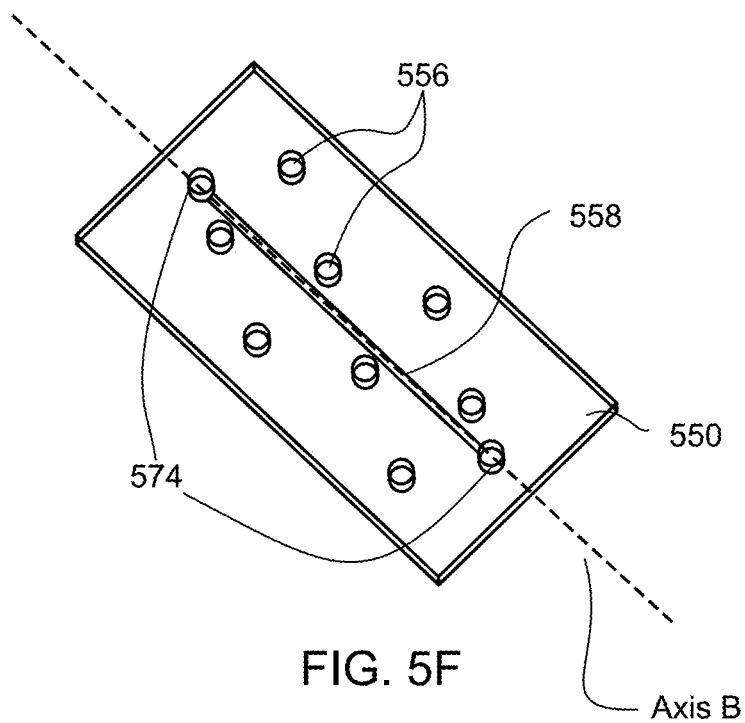
Figure 5G:
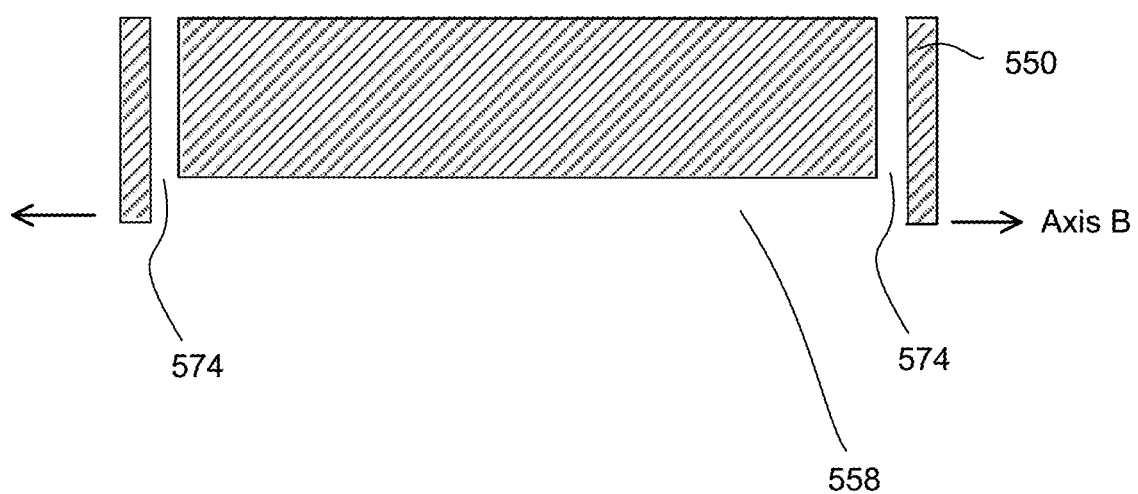

FIGS. 5F and 5G illustrate a cover 550 for the array nanopore device, according to one embodiment. As illustrated in FIG. 5F, the cover 550 includes a single shared channel 558 that runs perpendicular to the multiple channels 508 of the first insulating layer 510. The cover 550 further includes multiple holes that penetrate through the cover 550. More specifically, a pair of holes 574 are located at the distal ends of the shared channel 558 of the cover 550. Additional holes 556 are positioned to substantially align with the reservoirs 515 of the first insulating layer 510. As depicted in FIG. 5F, the shared channel 558 runs in between each pair of holes that correspond to a pair of reservoirs 515 of a channel 508 of the first insulating layer 510.

FIG. 5G illustrates a cross section for the cover 550, along an axis B running through the shared channel 558 as shown in FIG. 5F. At either end of the shared channel 558, a hole 574 penetrates through the cover 550.

Figure 5H:
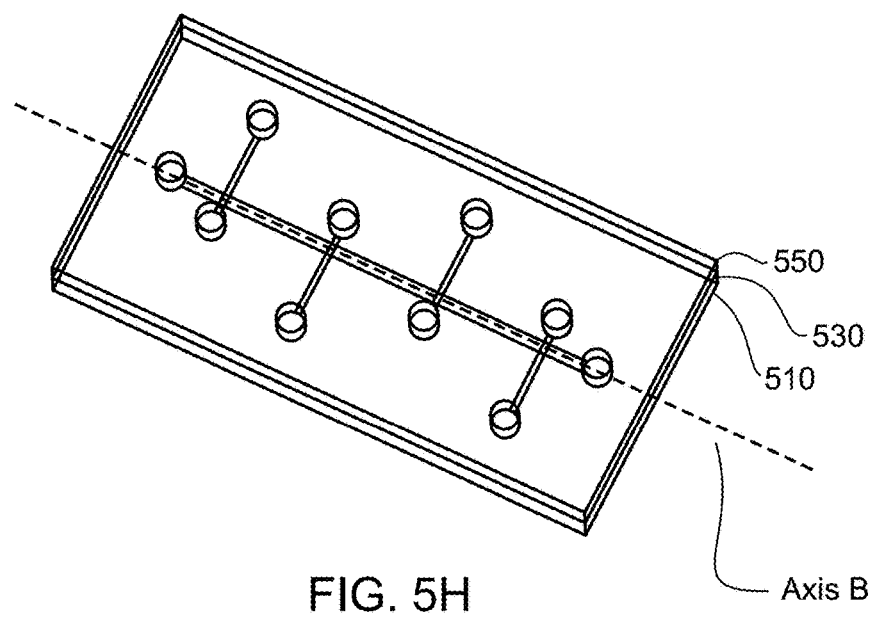
Figure 5I:
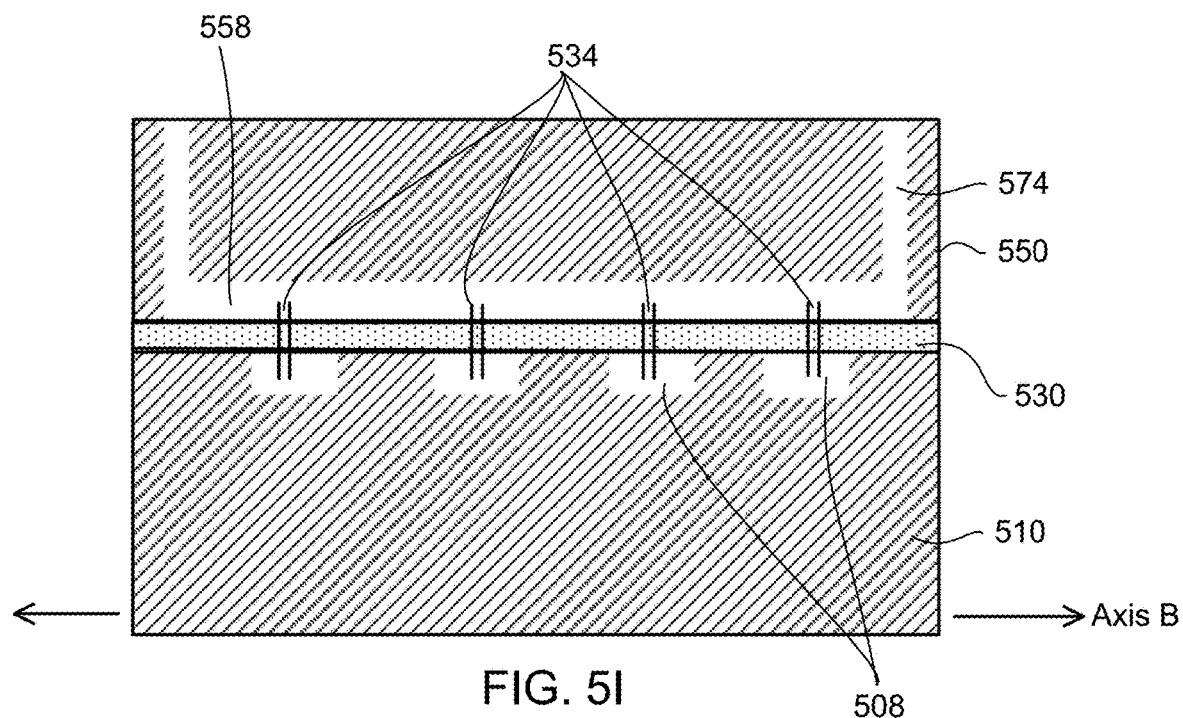

FIGS. 5H and 5I are a perspective and an array view, respectively, of the array nanopore device 500 after attachment of the cover 550, according to one embodiment. The cover 550 can be bonded using methods described previously in reference to FIGS. 3L and 3M. The shared channel 558 in the cover 450 is positioned to align with the locations of the nanopores 534 in the membrane layer 530. As such, each nanopore 534 fluidically connects a corresponding channel 508 to the shared channel 558 in the cover 550.

In operation, the shared channel 558 acts as the ground. Reagents are added to the shared channel 558 through the holes 574 of the cover 550. The other four orthogonal channels 508 in the first insulating layer 510 are used to apply voltage and/or detect impedance/current changes through corresponding nanopores 534.

VI. MECHANICAL ROBUSTNESS IMPLEMENTATION

Any of the different nanopore devices described in Sections I, II, III, IV, and V above may employ additional support structures to improve the mechanical robustness of the nanopore device.

Figure 6A:
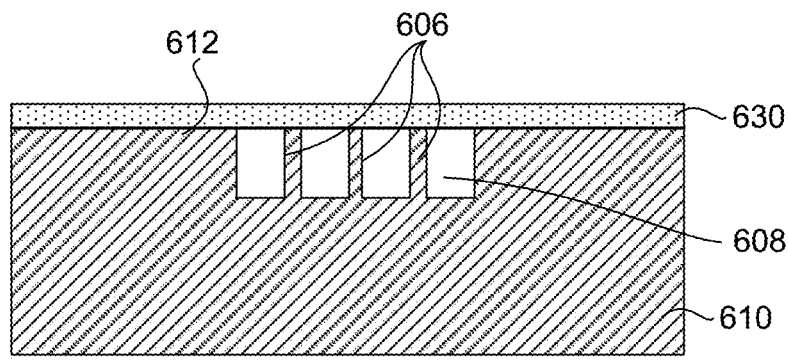
FIGS. 6A-6C illustrate structural enhancements to improve the mechanical robustness of a nanopore device, according to one embodiment.

FIG. 6A illustrate a modified first insulating layer 610 including a post array structure 606, according to one embodiment. The posts 606 in the array structure are narrow in both radius or length and width dimensions, hence the designation "posts." In one embodiment, the posts have a radius/length/width of 2 µm. The posts 606 are the same height as the non-channel outer surface 612 of the first insulating layer 610 so that they come into contact with the membrane layer 630 when the membrane layer 630 is bonded to the first insulating layer 610. Consequently, the posts 606 serve to provide mechanical support to the membrane layer 630 within the channel 608 by distributing stress.

Figure 6B:
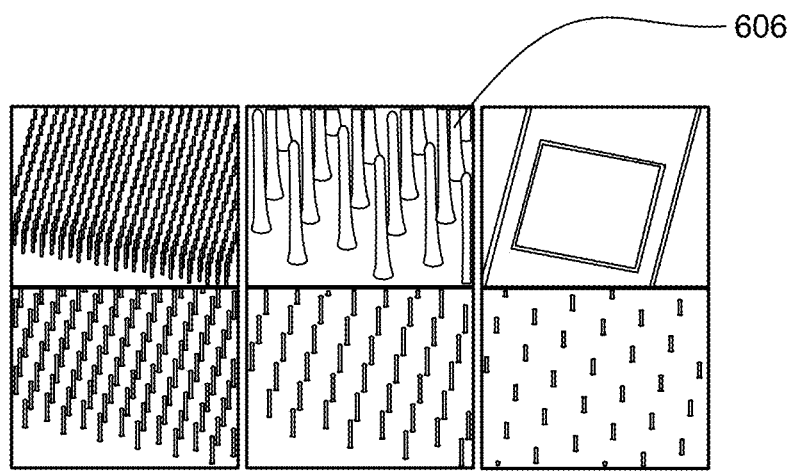

FIG. 6B illustrates an perspective view of posts 606 in an example channel 608, according to one embodiment. The posts 608 are made at the same time the channel 608 is created by leaving some regions of the channel 608 of the first insulating layer 610 un-etched.

Figure 6C:
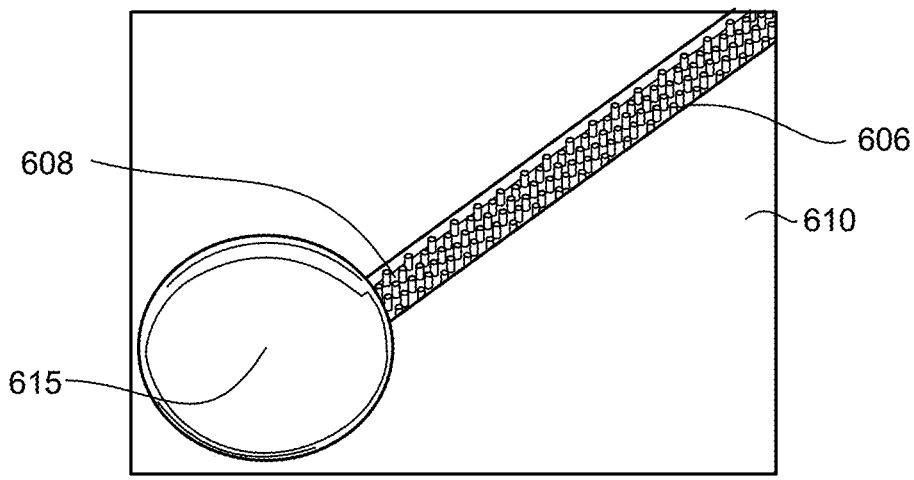

FIG. 6C illustrates a perspective view of a channel 608 in a first insulating layer 610 including posts 606, according to one embodiment. The posts 606 are formed in the "center" portion of the channel 608, that is, the portions of the channel 608 not located in the distal reservoir 615 located at either end of a channel 608. This is because these portions are used for other purposes, such as filling reagents through the reservoir 615, and adding posts 606 here would interfere with the ability of the user to carry out these tasks. Further, any additional mechanical robustness gained through the use of posts 606 in these areas would be minimal.

VII. OVERALL SYSTEM

Figure 7:
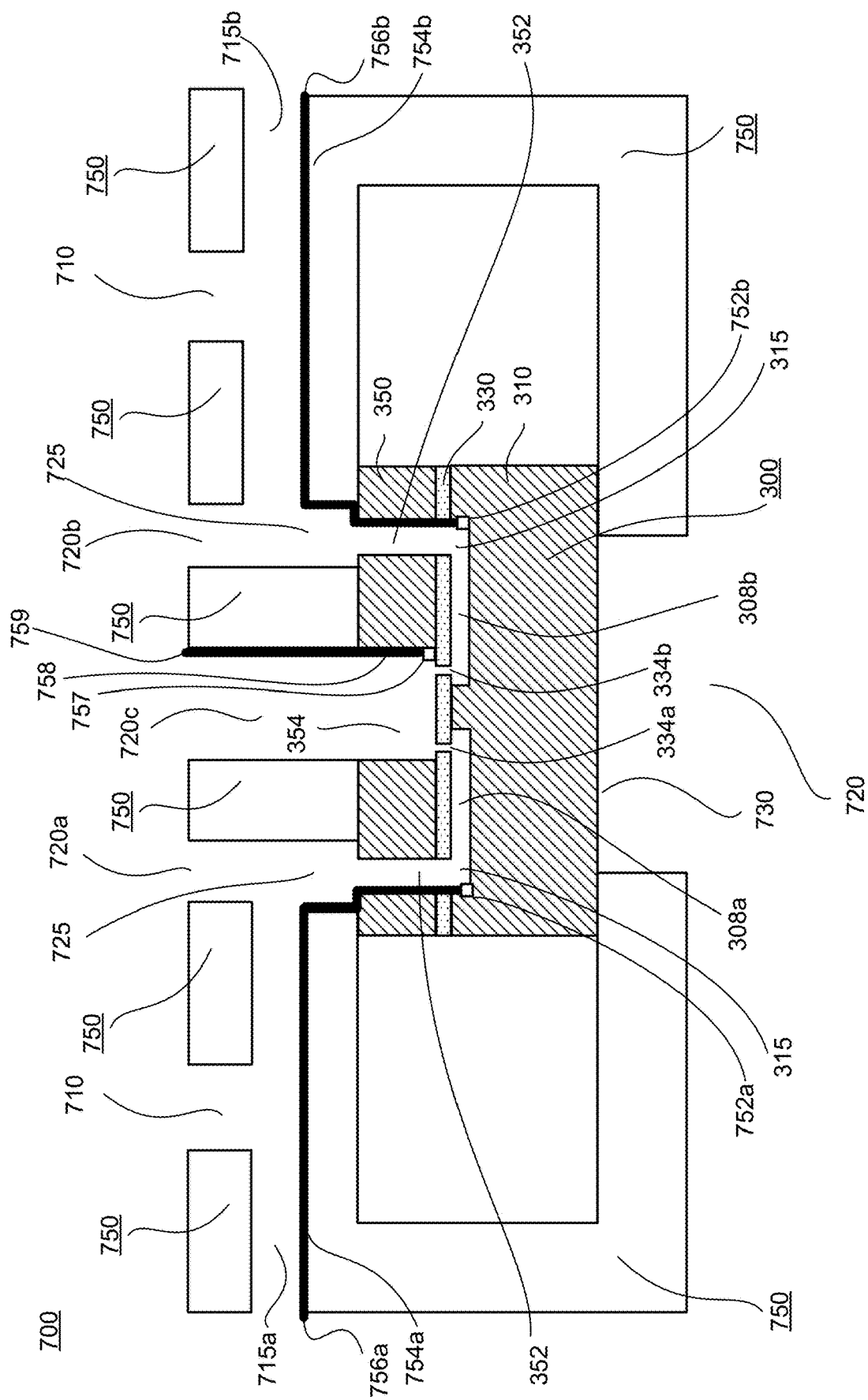
FIG. 7 illustrates a cross sectional view of a measurement system that includes a nanopore device within a flow-cell housing, according to one embodiment.

FIG. 7 illustrates a cross sectional view of a measurement system 700 that includes a nanopore device 300 within a flow-cell housing 750, according to one embodiment. In other embodiments, the nanopore device 400 described in FIG. 4A-4U or the nanopore device 500 described in FIG. 5A-5I can be mounted within the flow-cell housing 750 shown in FIG. 7.

As shown in FIG. 7, the flow-cell housing 750 interfaces with the nanopore device 300 such that the nanopore device 300 is translationally and rotationally affixed relative to the flow-cell housing 750. For example, the flow-cell housing 750 may be configured to clamp the nanopore device 300 in place. As depicted in FIG. 7, the flow-cell housing 750 interfaces with the nanopore device 300 through the cover 350 of the nanopore device 300 and the first insulating layer 310 of the nanopore device 300. The flow-cell housing 750 may apply an upward force on the first insulating layer 310 of the nanopore device 300 and a downward force on the cover 350 such that the nanopore device 300 is clamped in place.

The flow-cell housing 750 may be configured with various openings that enable the detection of a translocation event through a nanopore 334 of the nanopore device 300. More specifically, the flow-cell housing 750 can include ports 720. As shown in FIG. 7, ports 720*a* and 720*b* are substantially aligned with holes 352 of the cover 350 (which is further aligned with a reservoir of the first insulating layer 310). Additionally, port 720*c* is substantially aligned with the center hole 354 of the cover which resides above the nanopores 334 in the membrane layer 330. A solution (e.g., a buffer solution such as 1M lithium chloride) can be provided through the ports 720*a* and 720*b* of the flow-cell housing 750 to enter into the corresponding hole 352 of the cover 350 of the nanopore device 300. Thus, this solution provided through a port 720*a* or 720*b* corresponding to a hole 352 enters into the channel 308*a* and 308*b* of the nanopore device 300, respectively. Additionally, a solution provided through a port 720*c* corresponding to the center hole 354 resides in contact with the membrane layer 330 and the nanopores 334 of the nanopore device 300. This solution in the nanopore device 300 provided through port 720*c* will be hereafter referred to as the common reservoir. The ports 720 of the flow-cell housing 750 are sealable such that the solution provided through the ports into the nanopore device 300 can remain sealed within the fluidic connections.

In some embodiments, the flow-cell housing 750 may also include inlets 710 that are each configured to receive an external pressure. As an example, the inlets 710 can each couple with a tube or pipe that is further coupled to a gas source (e.g., a gas tank). The gas may be an inert gas such as nitrogen. Furthermore, the inlets 710 can be configured to direct the received external pressure to a channel 308. For example, as shown in FIG. 7, the inlets 710 may lead to walls of the flow-cell housing 700 that direct the external pressure to the channel 308. Therefore, if a solution is added through port 720*a* or 720*b* into the hole 352 of the cover 350, a gas provided through the inlet 710 exerts a pressure that forces the added solution to flow through the channel 308 to the nanopore 344.

In some embodiments, the flow-cell housing 750 does not include the inlets 710 when an external input is not necessary. For example, in some scenarios, the channels 308 of the nanopore device 300 may be appropriately designed such that when a solution is provided through a port into a hole 352, the capillary action of the solution within the channels 308 is sufficient to flow the solution through the channel 308.

Generally, the flow-cell housing 750 includes inlets 710 when the nanopore device 300 possesses channels 308 that have a width that is below a threshold width. In this scenario, capillary forces are not sufficient to drive fluid flow through these channels 308 that have a width below a threshold width. As another example, the flow-cell housing 750 includes inlets 710 when the nanopore device 300 possesses above a threshold density of channels 308. In this scenario, fluid is unable to fully flow through all the channels 308 and therefore, an inlet 710 for receiving an external pressure is necessary. Alternatively, the flow-cell housing 750 need not include inlets 710 when the nanopore device 300 possesses channels 308 above a threshold width or below a threshold density.

The flow-cell housing 750 further include slots 715 that are configured to receive electrodes that are designed to apply a voltage and measure a current in the solution in the nanopore device 300. As an example, an electrode 752 may enter through a slot 715 and reside in contact with the solution within the reservoir, which is the distal end of a channel 308, of the first insulating layer 310. Specifically, a first electrode that is in contact with the solution through slot 715*a* can apply a voltage and measure a current across a nanopore 334*a*, provided that another electrode resides in the center hole 354 that serves as a ground measurement. Similarly, a second electrode that is in contact with the solution through slot 715*b* can apply a voltage and measure a current across nanopore 334*b*, provided that another electrode resides in the center hole 354 that serves as a ground measurement.

As an example, the electrodes 752 (e.g., objecting residing in the reservoir 315 in FIG. 7) may be a metal (e.g., silver chloride Ag/AgCl electrode). The electrode 752 is in contact with a conductive trace 754 that is composed of a conductive metal (e.g., gold). The trace 754 can be deposited on the surface of the reservoir 315, the membrane layer 330 and the cover 350. The trace 754 may terminate on an external surface of the flow-cell housing. As such, the terminal end 756, which may be embodied as a contact pad, can be contacted by an amplifier that measures impedance changes and applies voltages through the electrode 752 to the respective channels 308. In some embodiments, the electrode 752 need not be in contact with a trace 754 deposited on the surfaces of each of the reservoir 315, the membrane layer 310, the cover 350, and the flow-cell housing 750. Namely, the electrode 752 can be in contact with a physically suspended conductive wire that enters through the slot 715.

In some embodiments, the port 720*c* corresponding to the center hole 354 is also configured to receive an electrode 757 that remains in contact with the solution in the center hole 354. As such, the electrode 757 can apply a voltage or to the solution measure an impedance across a nanopore 334. The common reservoir may serve as the ground. As shown in FIG. 7, the electrode 757 in the center hole 354 may also be in contact with a trace 758 that is deposited on the surface of the cover and the flow-cell housing 750. Therefore, the trace 758 of such an electrode 757 can terminate on an external surface 759 of the flow-cell housing 750 such that an amplifier in contact with the terminal end of the trace can measure impedance changes and apply voltages through the electrode 757 to the solution in the center hole 354.

As depicted in FIG. 7, a slot 715, an inlet 710, and one of the sealable ports 720a or 720b each lead to a common cavity space 725 of the flow-cell housing. The common cavity space 725 is located above the hole 352 of the cover 350 and is therefore, in fluidic connection with the channel 308 through a reservoir 315 located at the distal end of the channel 308. Therefore, each of the port 720a or 720b, the inlet 710, and the slot 715 may be configured to ensure that each of their inputs (e.g., solution through port 720a or 720b, external pressure through inlet 710, and electrode through 715) are unidirectional and enter through the common cavity space 725 into the nanopore device 300. For example, when solution is provided through a port 720a or 720b, the inlet 710 and slot 715 are sealed such that the solution only enters into the nanopore device 300. Similarly, when external pressure is provided through the inlet 710, the port 720a or 720b and the slot 715 are each sealed such that the external pressure is exerted on the solution in the reservoir 315 and channel 308 of the nanopore device 300.

The flow-cell housing 750 further includes an aperture 720 through which an optical microscope can be situated to image the nanopore device 300. Namely, a lens of the optical microscope can reside within the aperture 720 in contact with a bottom surface 730 of the first insulating layer 310 of the nanopore device 300. In this scenario, the first insulating layer 310 may be a transparent or semi-transparent layer that minimally obstructs the passage of light that is emitted by and captured by the optical microscope. The optical microscope can be an inverted microscope that images the flow of solution through the channels 308 of the nanopore device 300. In some embodiments, the optical microscope is a fluorescent microscope that is able to capture fluorescently tagged molecules (e.g., fluorescently tagged DNA) that is flowing through the channels 308 of the nanopore device 300.

Overall, the flow-cell housing 750 achieves several purposes. First, the flow-cell housing 750 enables the handling and manipulation of a nanopore device 300 that, in may embodiments, may be difficult to manually handle due to its small size. Second, the flow-cell housing 750 facilitates the introduction of solution through each of the channels 308. In certain embodiments, a nanopore device 300 may have a high density of channels and as such, the flow-cell housing 750 can ensure that solution flows through all channels through the employment of the previously described external pressure.

However, in various embodiments, the measurement system 700 need not include the flow-cell housing 750 because a nanopore device 300 can be manually handled and fluid can be readily flowed through the channels 308 of the nanopore device 300. Specifically, if the nanopore device 300 is larger than a threshold size (e.g., on the centimeter scale or larger), then the nanopore device 300 can be manually manipulated without the need for a flow-cell housing 750. Also, as previously described, the channel 308 geometry of the nanopore device 300 may be sufficient to enable solution flow through the channels due to capillary action. In this example, solution and/or reagents can be manually pipetted into the reservoir 315 and channels 308 of the nanopore device 300 without the need for the flow-cell housing 750. In another embodiment, elements of an injection device can inject solution and/or samples into the reservoir 315 and channels 308 of the nanopore device 300 as opposed. Additionally, electrodes may be manually placed into the reservoirs 315 without the need for the flow-cell housing 750.

Figure 8C:
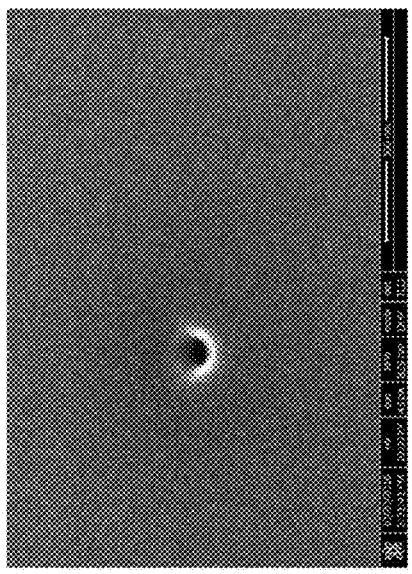
FIG. 8A-8D illustrate nanopore images and current measurements corresponding to a DNA translocating event through a nanopore of an example nanopore device.
Figure 8D:
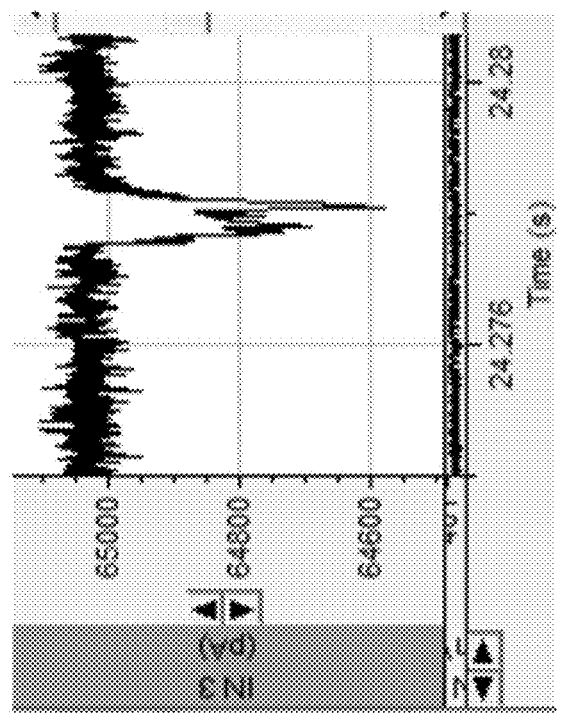
Figure 8A:
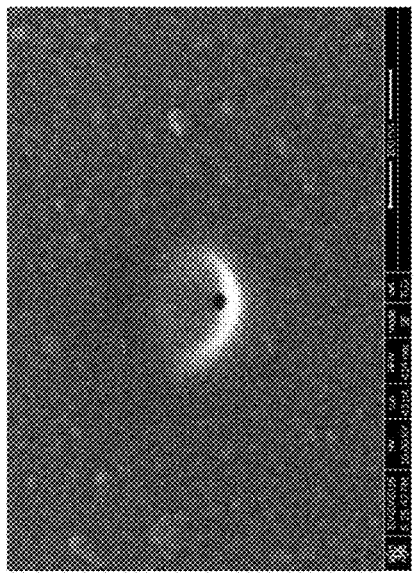
Figure 8B:
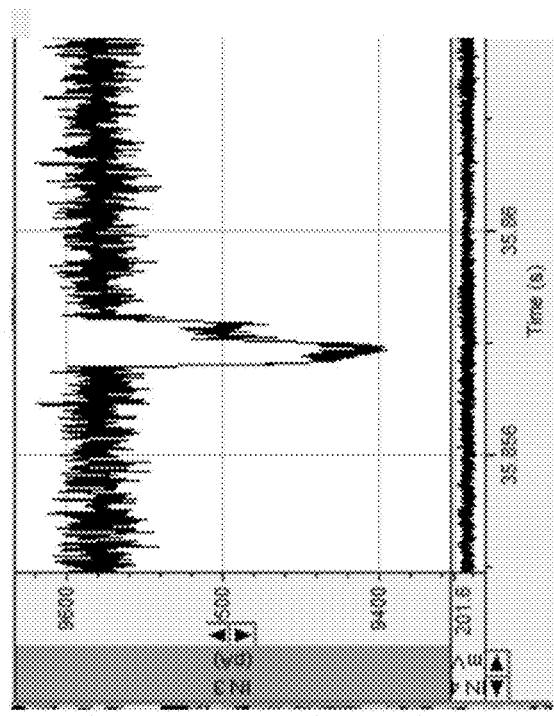

VIII. EXAMPLES a. Example 1: Detection of a Molecular Translocation Event Across a Nanopore FIGS. 8A and 8C each depict an example nanopore in a membrane layer of an example nanopore device. More specifically, the nanopore depicted in FIGS. 8A and 8C correspond to the nanopores 334 shown in the overall system of FIG. 7, for example a nanopore device built according to the process of Section III. Specifically, the membrane layer is thinned prior to the generation of the nanopores in the membrane layer. FIGS. 8B and 8D depict current measurements corresponding to a translocation event through the nanopores depicted in FIGS. 8A and 8C, respectively. A translocation event refers to a molecule passing through a nanopore. In one embodiment, the translocation event involves a DNA molecule (5.6 kilobase pairs in length) that passes through the nanopore.

More specifically, FIG. 8B illustrates a current measurement as a DNA molecule passes through a nanopore from the common reservoir to the individual channel of the nanopore device. Referring to FIG. 7, this refers to the translocation of a DNA molecule from the hole 354 of the cover 350 through a nanopore 334 into a channel 308. The example shown in FIG. 8B corresponds to an applied voltage of 200 mV across the 9.22 nm nanopore of FIG. 8A. The occurrence of the translocation is indicated by the transient change in current (in picoamps) from approximately 9600 pA to 9400 pA between 35.856 and 35.86 seconds.

FIG. 8D illustrates a current measurement as a DNA molecule translocates through a nanopore in an opposite direction than that of FIG. 8B. Namely, the DNA molecule translocates through a nanopore from an individual channel of the nanopore device to the common reservoir. The example shown in FIG. 8D corresponds to an applied voltage of 400 mV across the 32.89 nm nanopore of FIG. 8B. The occurrence of the translocation is indicated by the transient change in current (in picoamps) from approximately 65000 pA to 64600 pA between 24.276 and 24.28 seconds. The difference in current (pA) values observed in FIG. 8B and FIG. 8D arises from the different characteristics of the nanopores (e.g., diameter size) and applied voltage.

The examples of FIGS. 8A-8D illustrate that a translocation event can be adequately detected based on a measurement of a change in the current, regardless of the direction of translocation. As such, the nanopore device (with the nanopores) can be used to detect a translocation event of a molecule (e.g., DNA, amino acid, and the like) which can be used in sequence to determine the molecule itself, or make some other form of derived deduction.

Figure 9A:
FIG. 9A-9B illustrate measurements corresponding to Lambda DNA translocating events through a nanopore of an example nanopore device.
Figure 9B:
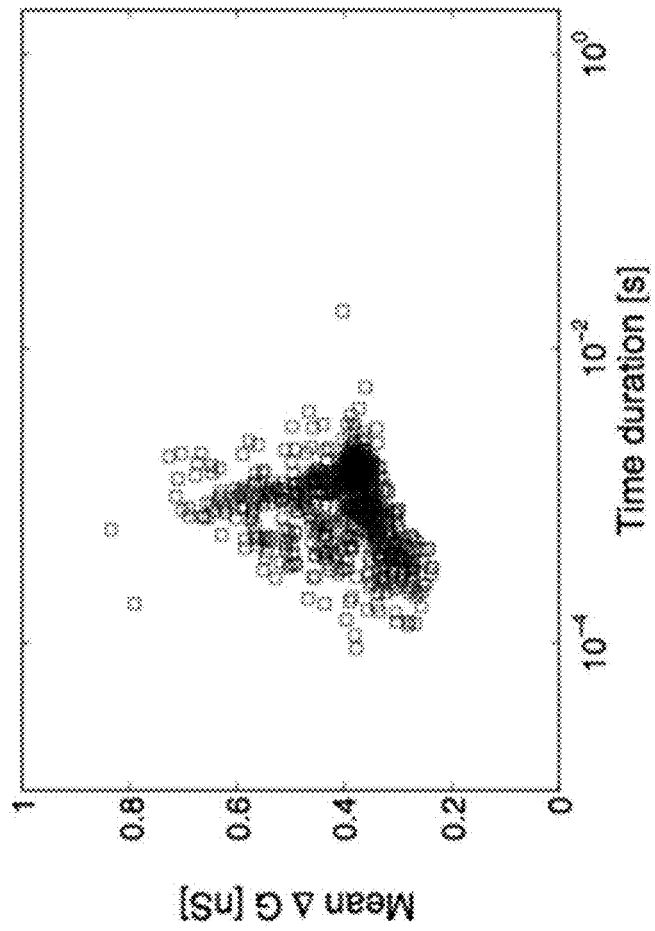

FIG. 9A-9B illustrate example measurements corresponding to Lambda DNA translocating events through a nanopore of an example nanopore device built according to the process of Section III. In these examples, Lambda DNA molecules translocate from the common reservoir to the individual channel through a ~30 nm diameter nanopore under an applied voltage of 200 mV.

Specifically, FIG. 9A depicts an example current measurement for a single Lambda DNA translocation event through the example nanopore referenced above. For this translocation event, the average conductance shift ΔG, which is the average change in current divided by the applied voltage, is 0.4 nano Siemens (nS) for a duration of 1.5 ms.

FIG. 9B depicts a scatter plot that includes example data from various Lambda DNA translocation events for this example nanopore and corresponding nanopore device. Specifically, the scatter plot depicts the mean conductance shift (ΔG) as a function of time duration. As shown in the scatter plot, the Lambda DNA translocation events correspond to an average ΔG between 0.2 and 0.8 nano Siemens for a duration between 0.1 milliseconds to 10 milliseconds.

b. Example 2: Improved Noise Performance of a Nanopore Device

Figure 10:
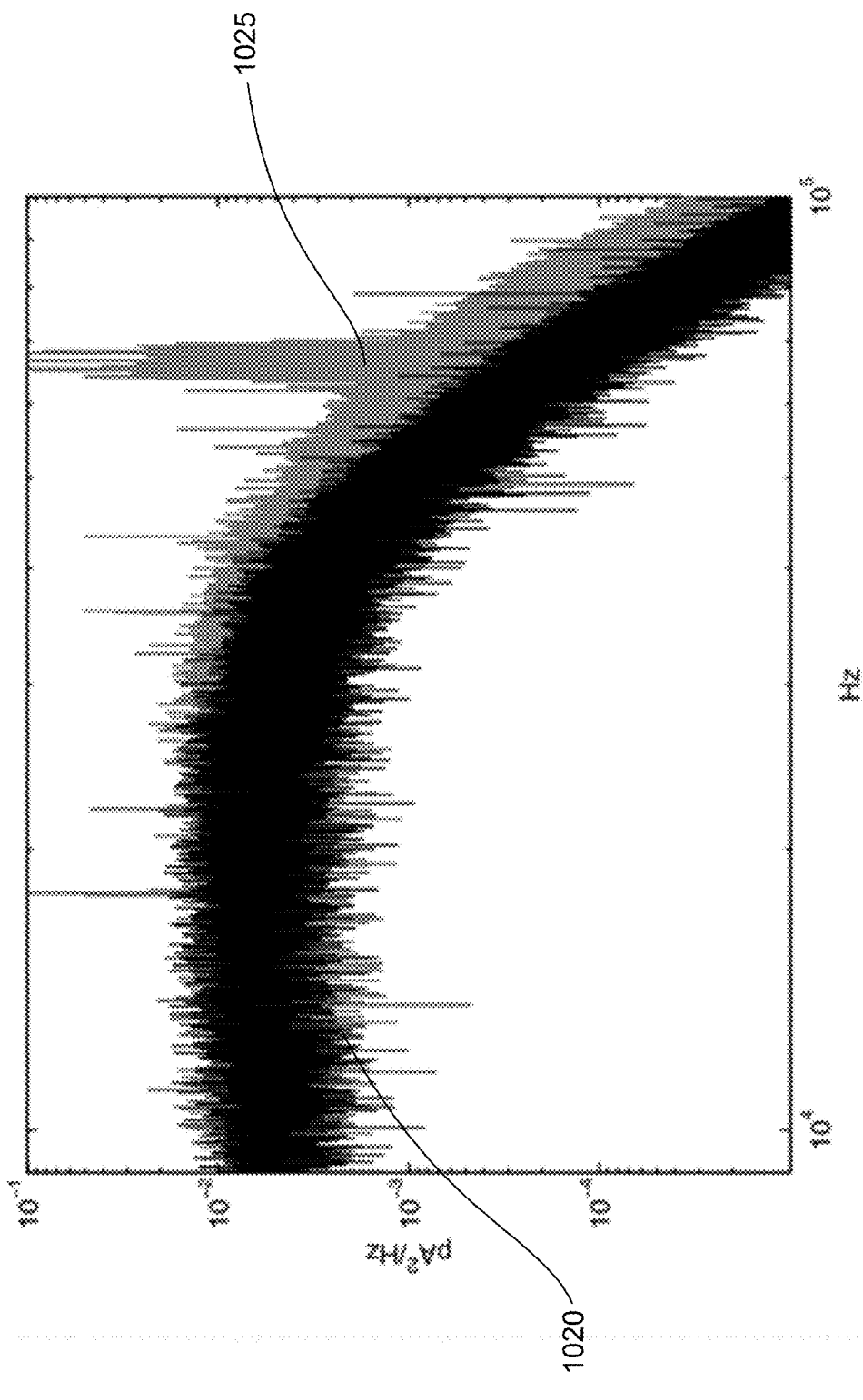
FIG. 10 depicts the noise performance of an example nanopore device in comparison to a silicon-based device.

FIG. 10 depicts the improved noise performance of a nanopore device 1020 in comparison to a silicon-based device 1025. The example nanopore device used to generate the data of FIG. 10 is the nanopore device 300 depicted in the FIG. 7 where the first insulating layer is composed of glass as generated according to the process described in Section III. This nanopore device includes a 9 nm diameter nanopore located within a thinned 50 nm portion of the membrane layer under the application of a 200 mV voltage. The silicon-based device includes layers of silicon, silicon nitride, and silicon dioxide and includes a 22 nm nanopore in a 30 nm silicon nitride layer. Further description for generation of a silicon-based device as used in this comparison example is described in Nanopore-based Technology, Methods in Molecular biology Vol. 870 (Humana Press, New York, 2012), p. 241.

FIG. 10 depicts the power spectral density (PSD) of the noise signal for each example device. The PSD noise estimates of each device were computed via Welch's method (Hamming window, 50% overlap) applied to 500,000 samples of the baseline current after subtracting the mean.

The nanopore device demonstrates a stronger ability to dampen the noise in higher frequencies (e.g., above 30 kHz) comparing to the silicon-based chip. Consequently, the root mean square (RMS), otherwise referred to as the noise standard deviation (sigma), is significantly lower for the nanopore device. At 30 kHz bandwidth, the RMS is 12 pA for the nanopore device, whereas the silicon-based device has a RMS of 18 pA. This demonstrates the superior noise performance of the nanopore device.

The aggregate (integrated) noise power is quantified by the RMS noise signal, and determines the sensing resolution limit of any device that detects a translocation event, including both of these example devices. The analog low-pass filter in a voltage clamp circuitry is used to attenuate high frequency noise, and the bandwidth of that filter is set to meet performance requirements. In particular, the bandwidth determines the temporal resolution limit, and the RMS at that bandwidth determines the amplitude resolution limit via the detection threshold. Specifically, one common approach is to set the detection threshold at 6 times the RMS (standard deviation) of the open channel signal. Further details regarding setting a detection threshold is described in Morin et al, "Nanopore-Based Target Sequence Detection," PloS One, 11(5):e0154426-21, May 2016, which is hereby incorporated in its entirety by reference.

Thus, in order to be detected, events must be long enough in duration (relative to the bandwidth rise time) and deep enough in attenuation (relative to detection threshold). Therefore, the lower the RMS at a given bandwidth, the better the sensing resolution. In FIG. 10, the RMS is 12 pA at 30 kHz bandwidth for the nanopore device, 50% better than the RMS of 18 pA at the same 30 kHz bandwidth for the silicon-based device. Therefore, the detection threshold is 72 pA below the baseline for the nanopore device, and 122 pA below the baseline for the silicon-based device. Thus, all translocation events with a depth between 72 pA and 112 pA would be missed using the silicon-based chip, but will be detected when using the nanopore device. For larger nanopore sizes (>20 nm diameter) this improved resolution can represent the difference between detecting a translocation event due to a target (e.g., circulating tumor DNA only 50-200 base pairs in length) and missing the event altogether.

c. Example 3: Combined Optical Imaging and Electrical Nanopore Sensing

Figure 11A:
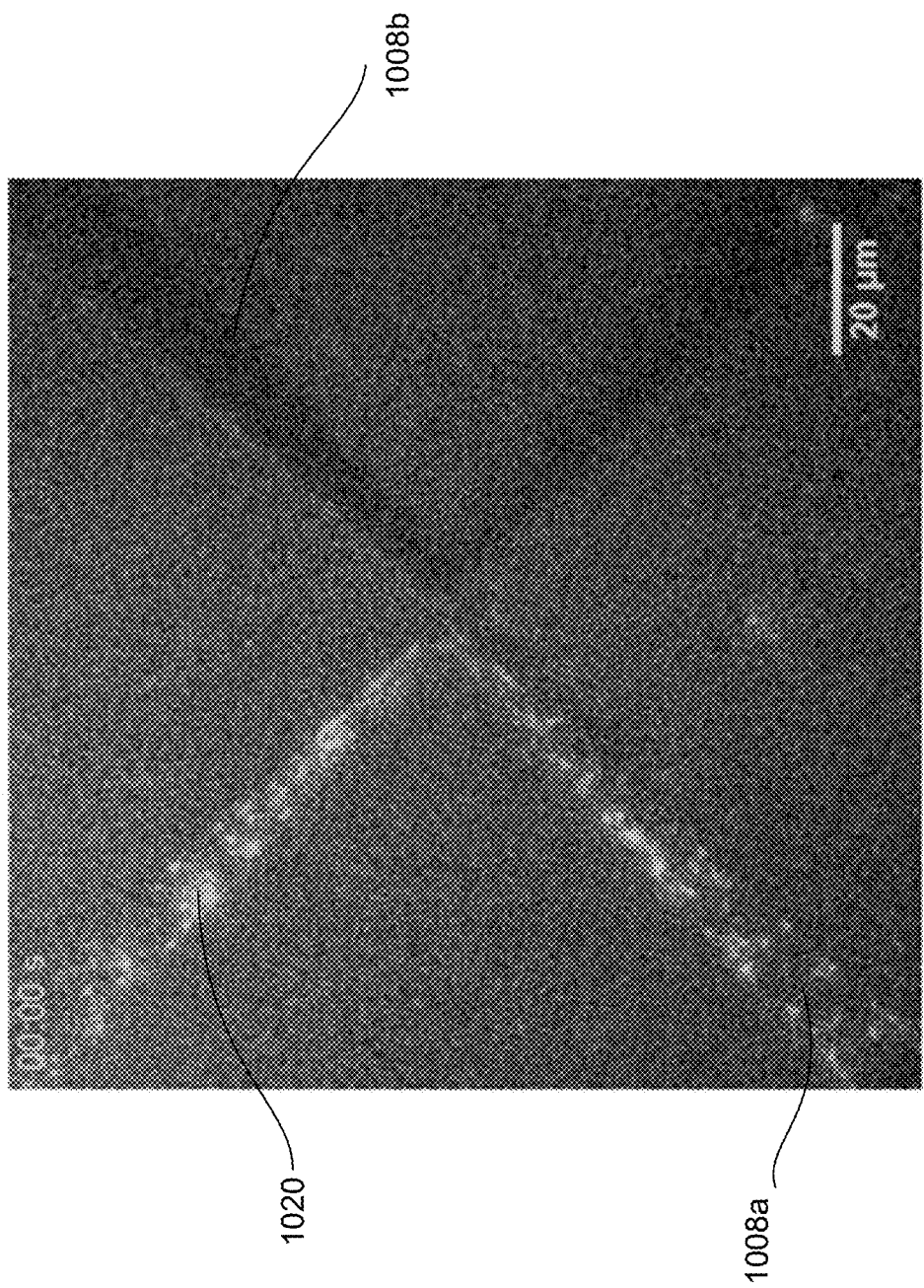

FIG. 11A-C depicts combined optical imaging and electrical nanopore sensing using a nanopore device fabricated through the method described in Section III. Specifically, FIG. 11A depicts an image of solution flowing through channels 1108 within the nanopore device captured by an inverted optical microscope located in the aperture 720 of the flow-cell housing 750. In conjunction with the optical imaging, as shown in FIG. 11B-C, an electrical signal amplifier records a time-varying electrical signal from one or more nanopores in the nanopore device.

As shown in FIG. 11A, fluorescently labeled, double stranded DNA (length of 5.6 kilobase pairs) is flowed through a channel 1008a which is captured by a fluorescent, optical microscope. An opposite channel 1008b remains empty or without fluorescently tagged molecules in this image. Other forms of optical imaging may also be performed such as light microscopy, electron microscopy, and the like.

FIG. 11B specifically depicts the voltage and current measurement across a first nanopore as a DNA (length of 5.6 kilobase pairs) translocates from a first channel into a common reservoir. Here, the applied voltage is 150 mV. The exploded inset depicts an enlarged view of the detected change in current corresponding to the translocation event (between 10 and 11 seconds). Simultaneously, the voltage and current measurement of a second nanopore is also monitored, as is shown in FIG. 11C. Here, the applied voltage is 300 mV. The exploded inset in FIG. 11C depicts a subsequent detected change in current (between 15-16 seconds) that corresponds to a DNA translocation event where the DNA translocates from the common reservoir to a second channel. Altogether, the resulting optical and electrical data may be used for genomic mapping, among other uses.

IX. ADDITIONAL CONSIDERATIONS

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

The invention claimed is:
1. A measurement system comprising:
   a nanopore device comprising:

an insulating substrate comprising one or more fluid channels formed into a surface of the insulating substrate, wherein the one or more fluid channels of the substrate includes an array of posts;
a cover comprising a center hole and a plurality of outer holes; and
a membrane layer positioned between the insulating substrate and the cover, a first surface of the membrane layer bonded to the surface of the substrate, the membrane layer comprising:
one or more nanopores that each fluidically connects one of the fluid channels of the insulating substrate to the center hole of the cover; and
a plurality of holes, wherein each hole in the membrane layer is substantially aligned with one of the plurality of outer holes of the cover, and
wherein the one or more fluid channels of the substrate includes an array of posts.

2. The system of claim 1 further comprising:
a flow-cell housing configured to affix a position of the nanopore device relative to the flow-cell housing.

3. The system of claim 2, wherein the flow-cell housing comprises:
a plurality of sealable ports, each sealable port configured to substantially align with one of the center hole or the plurality of outer holes of the cover;
at least one electrode, wherein one of the at least one electrode resides within a reservoir of one of the one or more fluid channels in the nanopore device; and
a slot through which one of the at least one electrode passes through.

4. The system of claim 3, wherein the one of the at least one electrode is in contact with a conductive trace that terminates on an external surface of the flow-cell housing.

5. The system of claim 4, wherein the one of the at least one electrode is a silver chloride electrode and wherein the conductive trace is gold metal.

6. The system of claim 3, wherein the flow-cell housing further comprises:
an aperture configured to receive an optical imaging device.

7. The system of claim 3, wherein the flow-cell housing further comprises an inlet configured to receive and direct an externally applied pressure to an end of at least one of the one or more fluid channels of the nanopore device.

8. The system of claim 7, wherein one of the plurality of sealable ports, the inlet, and the slot of the flow-cell housing lead to a common cavity of the flow-cell housing, the common cavity in fluidic connection with a fluid channel of the nanopore device.

9. The system of claim 1, wherein the membrane layer comprises:
a first portion that has a first thickness; and
a second portion that has a second thickness that is less than the first thickness, wherein the second portion is located above a portion of the one or more fluid channels.

10. The system of claim 9, wherein the first portion of the membrane layer has a thickness between 100-300 nm and wherein the second portion of the membrane layer has a thickness between 10-50 nm.

11. The system of claim 9, wherein each of one or more nanopores is generated in the second portion of the membrane layer.

12. The system of claim 1, wherein each of the one or more nanopores is between 5-50 nm in diameter.

13. The system of claim 1, wherein each of the one or more fluid channels of the substrate includes a reservoir at one end of the fluid channel, and wherein each reservoir is substantially aligned with a hole of the plurality of outer holes on the cover.

14. The system of claim 13, wherein each reservoir has a diameter between 100 µm and 1 mm.

15. The system of claim 1, wherein a depth of each of the one or more fluid channels on the surface of the substrate is between 0.1 to 10 µm.

16. The system of claim 1, wherein a first nanopore of the one or more nanopores fluidically connects a first fluid channel of the substrate to the center hole of the cover and a second nanopore of the one or more nanopores fluidically connects a second fluid channel of the substrate to the center hole of the cover.

17. The system of claim 1, wherein the system comprises a second fluid channel coupled to at least one of the one or more nanopores, and wherein a portion of a first fluid channel and a portion of the second fluid channel are parallel to each other.

18. The system of claim 17, wherein the system comprises a second fluid channel coupled to at least one of the one or more nanopores, and wherein the first fluid channel and the second fluid channel are closest to each other along the portion of the first fluid channel and the portion of the second fluid channel.

19. The system of claim 1, wherein the system comprises a second fluid channel coupled to at least one of the one or more nanopores, and wherein the first fluid channel and second fluid channel each form an elbow point.

20. The system of claim 19, wherein the first fluid channel and the second fluid channel of the nanopore device are closest in distance to each other at the elbow point of the first fluid channel and the elbow point of the second fluid channel.

21. The system of claim 20, wherein the elbow point of the first fluid channel is located at a midpoint of the first fluid channel and wherein the elbow point of the second fluid channel is located at a midpoint of the second fluid channel.

22. The system of claim 1, wherein the insulating substrate and the cover are each composed of an insulator selected from one of fused silica, sapphire, borosilicate glass, aluminosilicate glass, quartz, pyrex, or polydimethylsiloxane.

23. The system of claim 1, wherein the membrane layer is one of silicon nitride (SiN) or silica ($SiO_2$).

24. The system of claim 1, wherein the nanopore device further comprises:
a second membrane layer, wherein a first surface of the second membrane layer is bonded to a second surface of the membrane layer and a second surface of the second membrane layer is bonded to the cover, the second membrane layer comprising:
a fluid channel on the first surface of the second membrane layer; and
a nanopore located in the fluid channel of the second membrane, the nanopore of the second membrane being substantially aligned with one of the one or more nanopores of the membrane layer.

25. The system of claim 24, wherein the fluid channel of the second membrane layer is orthogonal to one of the one or more fluid channels of the insulating substrate.

* * * * *

UNITED STATES PATENT AND TRADEMARK OFFICE
CERTIFICATE OF CORRECTION

PATENT NO. : 10,488,394 B2
APPLICATION NO. : 16/083997
DATED : November 26, 2019
INVENTOR(S) : Xu Liu, Yuning Zhang and William B. Dunbar Page 1 of 1

It is certified that error appears in the above-identified patent and that said Letters Patent is hereby corrected as shown below:

In the Claims

Column 22, Line 49, after "silicon nitride," delete "(SiN)" and insert --SiNx--.

Signed and Sealed this
Third Day of March, 2020

Andrei Iancu
*Director of the United States Patent and Trademark Office*